US011879374B2

(12) United States Patent
Chitac et al.

(10) Patent No.: US 11,879,374 B2
(45) Date of Patent: Jan. 23, 2024

(54) STA-30, A NEW MEMBER OF THE SWY FAMILY OF MOLECULAR SIEVES, METHODS OF PREPARATION AND USE

(71) Applicant: Johnson Matthey Public Limited Company, London (GB)

(72) Inventors: Ruxandra Georgiana Chitac, St Andrews (GB); Nicholas McNamara, Wayne, PA (US); Alessandro Turrina, Billingham (GB); Paul Anthony Wright, St Andrews (GB)

(*) Notice: Subject to any disclaimer, the term of this patent is extended or adjusted under 35 U.S.C. 154(b) by 0 days.

(21) Appl. No.: 17/657,954

(22) Filed: Apr. 5, 2022

(65) Prior Publication Data

US 2022/0333519 A1 Oct. 20, 2022

Related U.S. Application Data

(60) Provisional application No. 63/201,088, filed on Apr. 12, 2021.

(51) Int. Cl.
| | | |
|---|---|---|
| *B01J 29/86* | (2006.01) | |
| *F01N 3/20* | (2006.01) | |
| *B01J 29/70* | (2006.01) | |
| *C07C 1/22* | (2006.01) | |
| *B01J 37/10* | (2006.01) | |
| *B01J 29/76* | (2006.01) | |
| *B01J 29/88* | (2006.01) | |
| *B01J 29/04* | (2006.01) | |
| *B01J 29/74* | (2006.01) | |
| *B01J 29/78* | (2006.01) | |
| *B01J 29/87* | (2006.01) | |
| *B01J 37/30* | (2006.01) | |
| *B01J 37/02* | (2006.01) | |
| *B01J 29/89* | (2006.01) | |
| *B01J 29/72* | (2006.01) | |

(52) U.S. Cl.
CPC .......... *F01N 3/2066* (2013.01); *B01J 29/046* (2013.01); *B01J 29/047* (2013.01); *B01J 29/048* (2013.01); *B01J 29/70* (2013.01); *B01J 29/7049* (2013.01); *B01J 29/72* (2013.01); *B01J 29/74* (2013.01); *B01J 29/76* (2013.01); *B01J 29/78* (2013.01); *B01J 29/86* (2013.01); *B01J 29/87* (2013.01); *B01J 29/88* (2013.01); *B01J 29/89* (2013.01); *B01J 37/0201* (2013.01); *B01J 37/10* (2013.01); *B01J 37/30* (2013.01); *C07C 1/22* (2013.01); *B01J 2229/18* (2013.01); *B01J 2229/183* (2013.01); *B01J 2229/186* (2013.01); *C07C 2529/70* (2013.01); *F01N 2570/14* (2013.01)

(58) Field of Classification Search
CPC .... B01J 37/0018; B01J 37/0201; B01J 37/10; B01J 37/30; B01J 2229/18; B01J 2229/183; B01J 2229/186; B01J 29/70; B01J 29/74; B01J 29/76; B01J 29/72; B01J 29/78; B01J 29/7049; B01J 29/046; B01J 29/047; B01J 29/048; B01J 29/86; B01J 29/87; B01J 29/88; B01J 29/89; C07C 2529/86; C07C 2529/87; C07C 2529/88; C07C 2529/89; C07C 2529/72; C07C 2529/74; C07C 2529/76; C07C 2529/78; C07C 2529/70; C07C 2529/06; C07C 2529/064; C07C 2529/068; C07C 2529/072; C07C 2529/076; C01B 39/02; C01B 39/04; C01B 39/06; C01B 39/065; C01B 39/08; C01B 39/082; C01B 39/085; C01B 39/087
USPC .......... 502/60, 61, 62, 73, 74; 423/700, 701, 423/702, 703, 704, 705, 706, 708
See application file for complete search history.

(56) References Cited

U.S. PATENT DOCUMENTS

| | | |
|---|---|---|
| 10,213,776 B2 | 2/2019 | Casci |
| 2017/0312743 A1 | 11/2017 | Casci et al. |

FOREIGN PATENT DOCUMENTS

| | | |
|---|---|---|
| EP | 3 445 716 A1 | 2/2019 |
| WO | 2017/182992 A1 | 10/2017 |
| WO | 2017/182995 A1 | 10/2017 |
| WO | WO 2021/099551 * | 5/2021 |

OTHER PUBLICATIONS

Turrina, A. et al., STA-20: An ABC-6 Zeotype Structure Prepared by Co-Templating and Solved via a Hypothetical Structure Database and STEM-ADF Imaging; Chemistry of Materials, 2017, vol. 29, pp. 2180-2190.

* cited by examiner

*Primary Examiner* — Elizabeth D Wood

(57) ABSTRACT

The present invention is directed to a method of preparing a molecular sieve of SWY framework type, denominated STA-30. STA-30 is synthesized using 1,4-diazabicyclo[2.2.2]octane, 1-azabicyclo[2.2.2]octane derivates and combinations thereof as structure directing agents. The resulting molecular sieve is useful as catalysts, particularly when used in combination with exchanged transition metal(s) for the Selective Catalytic Reduction (SCR) of NO.

20 Claims, 6 Drawing Sheets

STA-30, A NEW MEMBER OF THE SWY FAMILY OF MOLECULAR SIEVES, METHODS OF PREPARATION AND USE

FIELD OF INVENTION

The present invention relates to novel synthetic crystalline molecular sieve, denominated STA-30, its synthesis, and its use in a catalyst composition.

BACKGROUND

Zeolites are crystalline or quasi-crystalline aluminosilicates constructed of repeating $SiO_4$ and $AlO_4$ tetrahedral units linked by oxygen atoms at their vertices. The tetrahedral units and their linkages form various building units which can be arranged in numerous ways to form molecular frameworks, also known as topologies. Linking these frameworks in regular and repeating fashions creates to intra-crystalline cavities and channels of molecular dimensions, and thus micro-porosity in the zeolite. The spatial relationships arising from regularly repeating these molecular frameworks also give rise to different crystalline morphologies. More generally, other tetrahedrally coordinated framework structures, such as phosphates, can be used in combination with $AlO_4$ and optionally $SiO_4$ to form other types of molecular sieves such as silicoaluminophospates (SAPOs) or aluminophosphates (AlPOs).

Numerous types of synthetic zeolites have been synthesized and each has one or more unique frameworks based on the specific arrangement of its tetrahedral units. By the IUPAC nomenclature, each topological type is assigned a unique three-letter code (e.g., "CHA") by the International Zeolite Association (IZA) (http://www.iza-structure.org/databases/).

The process of zeolite crystallization cannot be adequately described merely by classical variables of reactant composition, temperature, and pressure. Crystallization also involves polymerization-depolymerization, solution-precipitation, nucleation-crystallization, and other complex phenomena encountered in aqueous colloidal dispersions. Specific zeolite topologies are predicated on the interaction of a structure directing agent (SDA), also referred to as a "template" or "templating agent" and the reaction mixture chemistry (e.g., all the other reaction parameters governing the reaction mixture, such as oxide composition, temperature, time, reagent type, and pH). SDAs are typically complex organic molecules which guide or direct the molecular shape and pattern of the zeolite's framework. Generally, the SDA serves to position hydrated silica and alumina and/or as a mold around which the zeolite crystals form. After the crystals are formed, the SDA is removed from the interior structure of the crystals, leaving a molecularly porous aluminosilicate cage.

Molecular sieves have numerous industrial applications, and molecular sieves having certain frameworks, such as CHA, and a certain composition, such as aluminosilicate, are known to be effective catalysts for treating combustion exhaust gas in industrial applications including internal combustion engines, gas turbines, coal-fired power plants, and the like. In one Example, nitrogen oxides ($NO_x$) in the exhaust gas may be controlled through a so-called selective catalytic reduction (SCR) process whereby $NO_x$ compounds in the exhaust gas are contacted with a reducing agent in the presence of a molecular sieve catalyst. In another Example, molecular sieves having the CHA framework type have found application in the conversion of methanol to olefins (MTO) catalysis.

U.S. Pat. No. 10,213,776 describes the silicoaluminophosphate molecular sieve STA-20 and its synthesis using alkyl amine, such as trimethylamine, and 1,6-(1,4-diazabicyclo[2.2.2]octane) hexyl cations as structure directing agents. The framework structure of STA-20 has been assigned a three-letter code SWY by the Structure Commission of the International Zeolite Association. According to the present invention, an aluminosilicate molecular sieve of SWY framework type, denominated STA-30, has now been synthesised using a selection of structure directing agents as describe herein. This new material is active for the Selective Catalytic Reduction (SCR) of $NO_x$.

SUMMARY OF THE INVENTION

In a first aspect of the invention, provided is a molecular sieve comprising a SWY type framework (STA-30), wherein the molecular sieve has a molar relationship: $Y_2O_3:(n)XO_2$ where Y is aluminum, boron, iron and/or gallium; X is silicon, tin, titanium and/or germanium. And n can be from about 5 to about 50, from about 10 to about 30, about 10 to about 25, about 10 to about 20, about 5 to about 15, or about 10 to about 15.

In a second aspect of the invention, provided is a method of synthesizing STA-30 which involves heating a reaction mixture comprising: a source of silicon oxide; a source of aluminum oxide; a source of alkali or alkaline earth metal cations; a source of a structure directing agent (SDA) comprising one or more 1,4-diazabicyclo[2.2.2]octane and 1-azabicyclo[2.2.2]octane dications derivates; a source of hydroxide ions comprising a quaternary ammonium compound; and water; under crystallization conditions for a sufficient period of time to form crystals of the aluminosilicate molecular sieve.

In a third aspect of the invention, provided is a composition prepared for manufacturing a molecular sieve having an STA-30 framework of the first aspect of the invention.

In a fourth aspect of the invention, provided is a catalytic composition comprising a molecular sieve of the first aspect of the invention.

In a fifth aspect of the invention, provided is a method for treating an exhaust gas from an engine by contacting the exhaust gas with an activated molecular sieve of the first aspect of the invention.

DETAILED DESCRIPTION OF THE INVENTION

Figure 1:
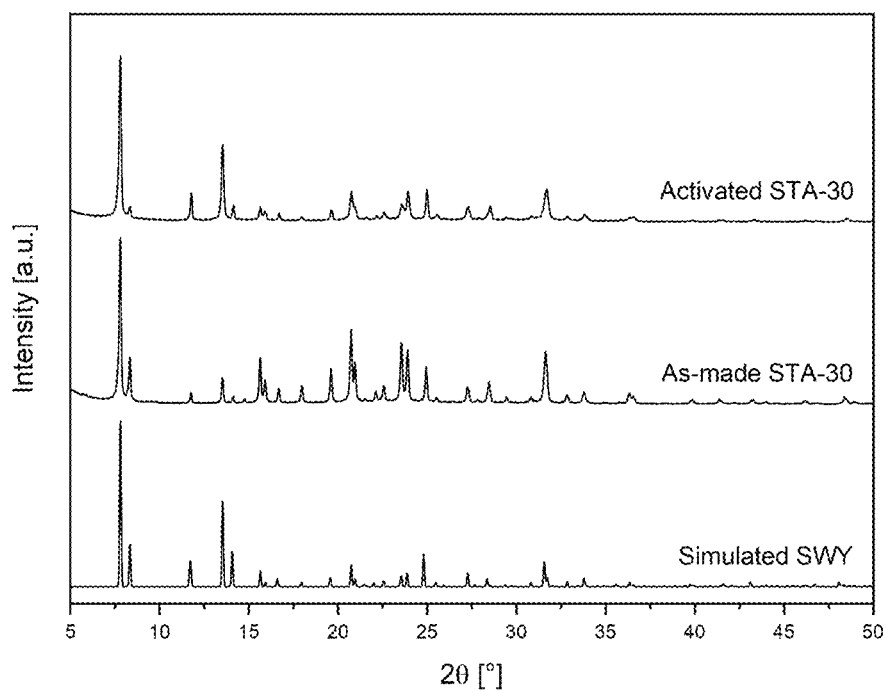
FIG. 1 shows powder X-ray diffraction (XRD) patterns of as-made and activated STA-30 from Example 1 compared to a simulated pattern for an ideal SWY framework type structure.

As used herein, the term "SWY" refers to the SWY type topology or framework as recognized by the International Zeolite Association (IZA) Structure Commission and the term "SWY zeolite" means an aluminosilicate in which the primary crystalline phase is SWY.

The term "as-made", as used herein, refers to a molecular sieve in its form after crystallization, prior to removal of the structure directing agent. The term "activated" refers to a molecular sieve in its H-form, after the removal of the structure directing agent and all or partial removal of the inorganic cations.

One aspect of the present invention is directed to a molecular sieve comprising a SWY type framework (STA-30), wherein the molecular sieve has a molar relationship: $Y_2O_3:(n)XO_2$; where Y is aluminum, boron, iron and/or gallium; X is silicon, tin, titanium and/or germanium. In some embodiments, Y can be aluminum. In other embodiments, X can be silicon. And n can be from about 5 to about 50, from about 10 to about 30, from about 10 to about 25, about 10 to about 20, about 5 to about 15, or about 10 to about 15.

In some embodiments, the molecular sieve has at least 95 mole percent, or even at least 97 mole percent of SWY framework. In certain embodiments, STA-30 is substantially free of other crystalline phases and frameworks. For example, STA-30 crystals synthesized by the methods described herein can be substantially free of frameworks such as MOR, FAU, ERI, OFF, and BEA. As used herein, the term "substantially free" means STA-30 contains less than one mole percent of a molecular sieve framework other than SWY.

In certain embodiments, the molecular sieve is substantially free of phosphorous within the framework, such as, have less than 1 ppm phosphorous, less than 0.5 ppm phosphorous or no detectable phosphorous.

The molecular sieve can be calcined, activated, or contains one of more structure directing agents (SDAs). Detailed SDA description is described in more detail in the second aspect of the present invention.

The as-made STA-30 molecular sieve can have XRD diffraction pattern containing at least the diffraction peaks listed in Table 1. And the activated STA-30 molecular sieve can have XRD diffraction pattern containing at least the diffraction peaks listed in Table 2.

TABLE 1

Characteristic Diffraction Peaks for as-made STA-30

| d-spacing [Å] | 2θ[a] [°] | I/I$_0$[b] [%] |
|---|---|---|
| 5.67 | 7.8 | vs |
| 5.31 | 8.3 | m |
| 3.78 | 11.8 | w |
| 3.29 | 13.5 | w |
| 3.16 | 14.1 | w |
| 2.86 | 15.6 | m |
| 2.81 | 15.9 | w |
| 2.68 | 16.7 | w |
| 2.30 | 19.6 | m |
| 2.18 | 20.7 | s |
| 2.16 | 20.9 | m |
| 2.01 | 22.6 | w |
| 1.93 | 23.5 | m |
| 1.90 | 23.9 | m |
| 1.83 | 24.9 | m |
| 1.68 | 27.3 | w |
| 1.62 | 28.5 | w |
| 1.47 | 31.6 | m |

[a] = ±0.3
[b] The relative intensity is based on the strongest line in the X-ray pattern which is assigned a value of 100. W (weak) is less than 20; M (medium) is between 20 and 40; S (strong) is between 40 and 60; and VS (very strong) is greater than 60.

TABLE 2

Characteristic Diffraction Peaks for activated STA-30

| d-spacing [Å] | 2θ[a] [°] | I/I$_0$[b] [%] |
|---|---|---|
| 5.67 | 7.8 | vs |
| 5.33 | 8.3 | w |
| 3.78 | 11.8 | w |
| 3.29 | 13.5 | s |
| 3.15 | 14.1 | w |
| 2.86 | 15.6 | w |
| 2.81 | 15.9 | w |
| 2.68 | 16.7 | w |
| 2.29 | 19.6 | w |
| 2.17 | 20.8 | w |
| 2.15 | 21.0 | w |
| 2.00 | 22.6 | w |
| 1.93 | 23.6 | w |
| 1.90 | 23.9 | w |
| 1.82 | 25.0 | w |
| 1.68 | 27.3 | w |
| 1.61 | 28.5 | w |
| 1.47 | 31.7 | m |

[a] = ±0.3
[b] The relative intensity is based on the strongest line in the X-ray pattern which is assigned a value of 100. W (weak) is less than 20; M (medium) is between 20 and 40; S (strong) is between 40 and 60; and VS (very strong) is greater than 60.

The X-ray powder diffraction patterns were determined by standard techniques. The radiation was the K-alpha/doublet of copper and a scintillation counter spectrometer with a strip-chart pen recorder was used. The peak heights, I, and their positions, in degrees, 2θ, where θ is the Bragg angle, were read from the spectrometer chart. From these measured values, the relative intensities, 100 I/I$_0$, where I$_0$ is the intensity of the strongest line or peak, and d, the interplanar spacing in Angstroms corresponding to the recorded lines, can be calculated. The X-ray diffraction pattern of Table 1 is characteristic of all species of STA-30 (template containing) family compositions. Minor variations in the diffraction pattern values in the tables or the figures can also result from variations in the organic compound used in the preparation, from variations in the silica-to-alumina mole ratio from sample to sample and from variation in the water content within the pores. In addition, the crystal size and morphology can also affect the shape and intensity of the peaks. Notwithstanding these minor perturbations, the basic crystal structures for the as-prepared condition and the activated condition remain substantially unchanged.

In certain embodiments, the STA-30 molecular sieve of the present invention can have a crystalline size of 0.1-10 μm, preferably, 0.1-5 μm; more preferably, 0.3-3 μm. In some embodiments, the STA-30 molecular sieve of the present invention can have one of the following morphologies: rice grain, spherical, or matchstick. In certain embodiments, the STA-30 molecular sieve of the present invention can have micropore volume of greater than 0.2 $cm^3/g$; preferably, at least 0.24 $cm^3/g$; more preferably, at least 0.28 $cm^3/g$. In some embodiments, the STA-30 molecular sieve of the present invention can have specific surface area of greater than 500 $m^2/g$; preferably, at least 650 $m^2/g$; more preferably, at least 740 $m^2/g$, measured by BET method.

In other embodiments, the molecular sieve can further comprise at least one extra-framework transition metal selected from the group consisting of Ag, Ce, Co, Cr, Cu, Fe, Ga, In, Ir, Mn, Mo, Ni, Pd, Pt, Re, Rh, Ru, Sn and Zn; preferably Cu, Fe, Co and Ni; more preferably Cu and Fe.

In a second aspect of the invention, provided is a method of synthesizing an aluminosilicate molecular sieve comprising a SWY type framework (STA-30) which involves heating a reaction mixture comprising: (a) at least one source of silicon oxide; (b) at least one source of aluminum oxide; (c) a source of alkali or alkaline earth metal cations; (d) a source of a structure directing agent (SDA) comprising one or more 1,4-diazabicyclo[2.2.2]octane and 1-azabicyclo[2.2.2]octane dications derivates; (e) a source of hydroxide ions comprising a alkyl quaternary ammonium compound; and (f) water; under crystallization conditions for a sufficient period of time to form crystals of the aluminosilicate molecular sieve. The method can further comprise recovering at least a portion of the aluminosilicate molecular sieve crystals from the reaction mixture.

A suitable structure directing agent comprises 1,4-diazabicyclo[2.2.2]octane, 1-azabicyclo[2.2.2]octane derivates and combinations thereof. For example a suitable 1,4-diazabicyclo[2.2.2]octane derivative is 1,6-(1,4-diazabicyclo[2.2.2]octane)hexyl, 1,7-(1,4-diazabicyclo[2.2.2]octane) heptyl, 1,8-(1,4-diazabicyclo[2.2.2]octane)octyl, 1,9-(1,4-diazabicyclo[2.2.2]octane)nonyl and 1,10-(1,4-diazabicyclo [2.2.2]octane)decyl. For example a suitable 1-azabicyclo [2.2.2]octane derivate is 1,6-(1-azabicyclo[2.2.2]octane) hexyl, 1,7-(1-azabicyclo[2.2.2]octane)heptyl, 1,8-(1-azabicyclo[2.2.2]octane)octyl, 1,9-(1-azabicyclo[2.2.2] octane)nonyl and 1,10-(1-azabicyclo[2.2.2]octane)decyl. The corresponding anions can be acetate, bicarbonate, bromide, carbonate, carboxylate, chloride, fluoride, hydroxide, iodide, sulfate and tetrafluoroborate, preferably bromide or hydroxide. More preferably the structure directing agent comprise 1,8-(1,4-diazabicyclo[2.2.2]octane)octyl dibromide, 1,8-(1-azabicyclo[2.2.2]octane)octyl dibromide, and combinations thereof.

In some embodiments, the suitable SDA can be preformed. In other embodiments, the suitable SDA can be made in-situ. For example, 1,4-diazabicyclo[2.2.2]octane and a dibromoalkane can be added in a 2:1 ratio to the gel. A suitable dibromoalkane is 1,7-dibromoheptane, 1,8-dibromooctane, 1,9-dibromononane and 1,10-dibromodecane.

The reaction mixture used to form STA-30 is preferably free or substantially free of phosphorous. STA-30 molecular sieves that are substantially free of framework phosphorous have less than 1 ppm phosphorous. STA-30 molecular sieves that are free of framework phosphorous have less than 0.5 ppm phosphorous or no detectable phosphorous. The molecular sieves of the present invention are not silicoaluminophosphates (SAPOs) and thus do not have an appreciable amount of phosphorous in their framework. That is, the molecular sieve frameworks do not have phosphorous as a regular repeating unit and/or do not have an amount of phosphorous that would affect the basic physical and/or chemical properties of the material, particularly with respect to the material's capacity to selectively reduce $NO_x$ over a broad temperature range.

Suitable silica sources include, without limitation, sodium silicate, fumed silica, silicates, precipitated silica, colloidal silica, silica gels, silica hydrogel, silicic acid, tetraalkyl orthosilicates, aluminosilicate zeolites having a SAR of about 2 to about 20; preferably, a SAR of about 5 to about 15, dealuminated zeolites such as dealuminated zeolite Y, and silicon hydroxides and alkoxides. Where zeolites are the silica source, the cation type may be at least one type selected from the group consisting of sodium type (Na type), proton type ($H^+$ type), and ammonium type ($NH_4$ type), where proton type is preferred. Silica sources resulting in a high relative yield are preferred.

Suitable alumina sources include sodium aluminate, aluminates, alumina, zeolites, aluminum colloids, boehmites, pseudo-boehmites, aluminum hydroxides, aluminum salts such as aluminum sulfate and alumina chloride, aluminum hydroxides and alkoxides (such as, aluminium isopropoxide), and alumina gels. Zeolite can be an aluminosilicate zeolite or derivative thereof, for example, faujasite (FAU), zeolite Y, and zeolite X, with FAU being most preferred. Preferably, the silica to alumina mole ratio of these zeolites should be from about 2 to about 20, more preferably, about 5 to about 15. Where zeolites are the alumina source, the cation type may be at least one type selected from the group consisting of sodium type (Na type), proton type ($H^+$ type), and ammonium type ($NH_4$ type), where proton type is preferred. Alumina sources resulting in a high relative yield are preferred.

In certain embodiments, zeolite can be used as both silica and alumina sources for the synthesis. In further embodiments, the reaction mixture may further comprise additional/optional silica and/or alumina sources (e.g., see Example 13).

The reaction mixture preferably includes a source of alkali or alkaline earth metal, such as one or more metals selected from sodium, potassium, cesium, lithium, and strontium. The form of alkali or alkaline earth metal may be, for example, hydroxides (e.g., sodium hydroxide (NaOH) or potassium hydroxide (KOH)), oxides (such as sodium oxide ($Na_2O$) or potassium oxide ($K_2O$)), carbonates, sulfates, nitrates, acetates, fluoride, chloride, bromide, iodide, silicates, aluminates, salts of carboxylic acids, and combinations of two or more of these. Preferred sources include alkali or alkaline earth metal hydroxide, such as NaOH, and alkali or alkaline earth metal oxide such as sodium oxide ($Na_2O$) and potassium oxide ($K_2O$). An alkali or alkaline earth metal may also be supplied via a zeolite when used as the alumina source. Additionally, when the silica source and the alumina source contain an alkali or alkaline earth metal, that alkali or alkaline earth metal may also serve as an alkali or alkaline earth metal source.

A suitable source of hydroxide ions includes alkyl quaternary ammonium compounds ($R_1R_2R_3R_4N^+OH^-$). The alkyl ammonium hydroxide can be a simple quaternary, where $R_{1-4}$ are all the same, or a more complex quaternary, where $R_{1-4}$ can be different. The quaternary ammonium hydroxide is preferably a lower alkyl ammonium hydroxide comprising one or more alkyl groups where each alkyl group can contain from 1 to 8 carbon atoms. Preferably the lower alkyl ammonium hydroxide is tetrabutylammonium hydroxide, tetraethylammonium hydroxide, tetrapropylammonium hydroxide, tetrapentylammonium hydroxide or tetrahexylammonium hydroxide. More preferably, the lower alkyl ammonium hydroxide is tetrabutylammonium hydroxide or tetrapropylammonium hydroxide.

In certain embodiments, one reagent might serve as more than one source. For example, the source of the SDA can also serve as the source of hydroxide ions. Suitable examples include 1,8-(1,4-diazabicyclo[2.2.2]octane)octyl dihydroxide, 1,7-(1,4-diazabicyclo[2.2.2]octane)heptyl dihydroxide, 1,9-(1,4-diazabicyclo[2.2.2]octane)nonyl dihydroxide.

Purified water may be used as the water, but each of the raw materials may also be used in the form of an aqueous solution.

In some embodiments, the reaction mixture can be essentially free of fluoride (e.g., less than 0.1 wt. % based on the reaction mixture.)

In certain embodiments, the reaction mixture has one or more of the following compositional molar ratios:

| | |
|---|---|
| $SiO_2/Y_2O_3$ | 10-100 |
| $Z_2O/XO_2$ | 0.01-1.0 |
| $SDA/XO_2$ | 0.01-0.8 |
| $OH/XO_2$ | 0.1-1.0 |
| $H_2O/XO_2$ | 8-80 |

X is silicon, tin, titanium and/or germanium; preferably, silicon
Y is aluminum, boron, iron and/or gallium; preferably, aluminum
Z=Na, K, Cs, and/or Li.

Preferably, the reaction mixture has one or more of the following compositional molar ratios:

| | |
|---|---|
| $SiO_2/Y_2O_3$ | 20-40 |
| $Z_2O/XO_2$ | 0.02-0.3 |
| $SDA/XO_2$ | 0.02-0.3 |
| $OH/XO_2$ | 0.4-0.7 |
| $H_2O/XO_2$ | 15-25 |

X is silicon, tin, titanium and/or germanium; preferably, silicon
Y is aluminum, boron, iron and/or gallium; preferably, aluminum
Z=Na, K, Cs, and/or Li.

In other embodiments, the reaction mixture has one or more of the following compositional molar ratios:

| | |
|---|---|
| $SiO_2/Y_2O_3$ | 10-100 |
| $ZO/XO_2$ | 0.01-1.0 |
| $SDA/XO_2$ | 0.01-0.8 |
| $OH/XO_2$ | 0.1-1.0 |
| $H_2O/XO_2$ | 8-80 |

X is silicon, tin, titanium and/or germanium; preferably, silicon
Y is aluminum, boron, iron and/or gallium; preferably, aluminum
Z=Sr and/or Ba.

Preferably, the reaction mixture has one or more of the following compositional molar ratios:

| | |
|---|---|
| $SiO_2/Y_2O_3$ | 20-40 |
| $ZO/XO_2$ | 0.03-0.3 |
| $SDA/XO_2$ | 0.02-0.3 |
| $OH/XO_2$ | 0.4-0.7 |
| $H_2O/XO_2$ | 15-25 |

X is silicon, tin, titanium and/or germanium; preferably, silicon
Y is aluminum, boron, iron and/or gallium; preferably, aluminum
Z=Sr and/or Ba.

The reaction mixture may also contain seeds of a molecular sieve material, such as STA-30 from a previous synthesis, desirably in an amount between 0.1 and 10% of the weight of silica in the composition.

Crystals of the STA-30 molecular sieves are formed by a hydrothermal synthesis process preferably performed in autoclaves or other hermetically sealed container, under static or dynamic conditions, at a temperature between 100° C. and 200° C., preferably from 120-180° C., and for period of time of between 0.5 day to 10 days, preferably from 2 days to 8 days, more preferably from 3 days to 7 days.

The precipitated molecular sieve crystals can be recovered by any well-known separation technique, such as, for example, decantation, filtration, ultrafiltration, centrifugation or any other solid-liquid separation technique, and combinations thereof. Preferred methods of separation include mechanical separation such as vacuum filtration. The recovered solids can then be rinsed with deionized or purified water and dried at an elevated temperature for several hours. The drying step can be performed under vacuum or at atmospheric pressure.

In the drying step, the water content is removed from the molecular sieve after the crystallization step or after the washing step. The conditions of the drying step are discretionary, but an example is drying the molecular sieve after the crystallization step or after the washing step by leaving the molecular sieve to stand for at least two hours, for example 4-24 hours, in an environment at a temperature not less than 50° C. and not greater than 150° C.

In a third aspect of the invention, provided is a composition that can be in the form of a solution, a colloidal dispersion (colloidal sol), gel, or paste, with a gel being preferred. The reaction mixture can be prepared either batch wise or in continuous. The composition comprising: (a) at least one source of aluminum oxide, (b) at least one source of silica, (c) a source of alkali or alkaline earth metal cations; (d) a source of a structure directing agent (SDA); (e) a source of hydroxide ions. Components (a)-(e) are the same as described in the second aspect above.

The composition preferably has the following composition:
  molar ratio of silica relative to alumina ($XO_2/Y_2O_3$ ratio) of about 10 to about 100, for example from about 20 and to about 40;
  molar ratio of alkali metal oxide relative to silica ($Z_2O/SiO_2$ ratio, Z=Na, K, Cs, Li) of about 0.01 to about 1.0, for example from about 0.02 to about 0.3 [or molar ratio of alkaline earth metal oxide relative to silica ($ZO/SiO_2$ ratio, Z=Sr) of about 0.01 to about 1.0, for example from about 0.03 to about 0.3];

molar ratio of SDA relative to silica (SDA/SiO$_2$ ratio) of about 0.01 to about 0.8, for example from about 0.02 to about 0.3;

molar ratio of OH relative to silica (OH/SiO$_2$ ratio) of about 0.1 to about 1.0, for example from about 0.4 to 0.7;

molar ratio of water (H$_2$O) relative to silica (H$_2$O/SiO$_2$ ratio) of about 8 to about 80, for example from about 15 to about 25.

The composition may also contain seeds of a molecular sieve material, such as STA-30 from a previous synthesis, desirably in an amount between 0.1 and 10% of the weight of silica in the composition.

Crystals of the STA-30 molecular sieves are formed by a hydrothermal synthesis process preferably performed in autoclaves or other hermetically sealed container, under static or dynamic conditions, at a temperature between 100° C. and 200° C., preferably from 120-180° C., and for period of time of between 0.5 days to 10 days, preferably from 2 days to 8 days, more preferably from 3 days to 7 days.

The precipitated molecular sieve crystals can be recovered by any well-known separation technique, such as, for example, decantation, filtration, ultrafiltration, centrifugation or any other solid-liquid separation technique, and combinations thereof. Preferred methods of separation include mechanical separation such as vacuum filtration. The recovered solids can then be rinsed with deionized or purified water and dried at an elevated temperature for several hours. The drying step can be performed under vacuum or at atmospheric pressure.

In the drying step, the water content is removed from the molecular sieve after the crystallization step or after the washing step. The conditions of the drying step are discretionary, but an example is drying the molecular sieve after the crystallization step or after the washing step by leaving the molecular sieve to stand for at least two hours, for example 4-24 hours, in an environment at a temperature not less than 50° C. and not greater than 150° C.

The synthesis methods described herein can produce STA-30 crystals with a high degree of purity, and preferably are phase pure. As used herein, the term "pure phase" means the STA-30 contains at least 95 mole percent of molecular sieve with the SWY topology. The phase purity can be determined by comparing the experimental X-ray powder diffraction pattern with the simulated pattern for an ideal SWY framework type structure (e.g., as shown in FIG. 1).

For example, STA-30 contains at least 95 mole percent, or even at least 97 mole percent of SWY frameworks. In certain embodiments, STA-30 is substantially free of other crystalline phases and frameworks. For example, STA-30 crystals synthesized by the methods described herein can be substantially free of frameworks such as MOR, FAU, ERI, OFF, and BEA. As used herein, the term "substantially free" means STA-30 contains less than one percent of a molecular sieve framework other than SWY.

Preferably, the overall process will have an overall yield on silica of ≥about 60%, for example ≥about 70%, ≥about 80%. Preferably, the overall process will have an overall yield on SDA of ≥about 40%, for example ≥about 60%, ≥about 80%, ≥about 90%, about 40-90%, about 40-60%, about 60-80%, about 80-90%, about 90-95%, or about 95-99%.

The process of the present invention may further comprise one or more steps to eliminate or extract the organic content retained inside the molecular sieve cavities (e.g., the SDA or by-products of the SDA), such as heating the material to a temperature greater than 25° C., preferably between 100° C. and 1000° C., more preferably between 400° C. and 600° C. for a period preferably ranging between about 1 to 50 hours, more preferably between 25 to 40 hours.

The molecular sieve material may be calcined, preferably in an oxygen containing environment, such as in air, at a temperature of about 450 to 600° C., preferably about 500-550° C., for a period from about 25-40 hours, for example from about 30 to 35 hours.

After crystallization, the STA-30 molecular sieves may have a metal ion such as an alkali metal ion at its ion exchange site. In an optional ion exchange step, the alkali metal ion is exchanged with a non-metal cation such as an ammonium ion (NH$_4^+$) or a proton (H$^+$). Ion exchange to an ammonium ion may be performed by mixing the molecular sieve into an ammonium chloride aqueous solution followed by stirring. Furthermore, ion exchange to a proton may be performed by ion-exchanging the molecular sieve with ammonia and calcining it.

As used herein, the SAR refers to the synthesized zeolite crystal and not to the starting synthesis gel. The SAR of the zeolites can be determined by conventional analysis. This ratio is intended to be as close as possible to the ratio in the rigid atomic framework of the zeolite crystal and to exclude silicon or aluminum in the binder or in cationic or other form within the channels. Since it may be difficult to directly measure the silica to alumina ratio (SAR) of the zeolite after it has been combined with a binder material, particularly an alumina binder, these silica to alumina ratios will be relative to the SAR zeolite per se, i.e., prior to combining the zeolite with the other catalyst components.

The STA-30 crystals can have a bulk silica-to-alumina ratio (SAR) of about 5 to about 50, for example, about 9 to about 25, about 10 to about 120, about 12 to about 15. As used herein, the term "bulk SAR" means the SAR of a crystal or sample of crystals taken as a whole. A zeolite's bulk SAR can be differentiated from its surface layer SAR.

The STA-30 crystals produced in accordance with this process can be uniform, with little to no twinning and/or multiple twinning or may form agglomerates.

The STA-30 crystals produced in accordance with the methods described herein can have a mean crystalline size of about 0.01 to about 10 μm, for example about 0.5 to about 5 μm, about 0.1 to about 3 μm, and about 1 to about 2 μm, where the endpoints may be included. Large crystals can be milled using a jet mill or other particle-on-particle milling technique to an average size of about 1.0 to about 1.5 micron to facilitate washcoating a slurry containing the catalyst to a substrate, such as a flow-through monolith.

The crystal size is based on individual crystals, preferably long rice-grain shaped crystals, in other embodiments, also could be spherical crystals or matchstick shaped crystals. Crystal size is the length of longest diagonal of the three-dimensional crystal. Direct measurement of the crystal size can be performed using microscopy methods, such as SEM and TEM. For example, measurement by SEM involves examining the morphology of materials at high magnifications (typically 1000× to 100,000×). The SEM method can be performed by distributing a representative portion of the zeolite powder on a suitable mount such that individual particles are reasonably evenly spread out across the field of view at 1000× to 100,000× magnification. From this population, a statistically significant sample of random individual crystals (e.g., 50-200) are examined and the longest diagonal of the individual crystals are measured and recorded. (Particles that are clearly large polycrystalline aggregates should not be included the measurements.

STA-30 molecular sieves can be used as a catalyst and/or adsorbent. In a preferred example of a catalyst composition, one or more catalytically active metals or metals that otherwise improve the performance of the catalyst composition (collectively, "enhancing metal") is exchanged into the STA-30. The exchange of enhancing metals can be accomplished post molecular sieve synthesis via incipient wetness, solid state ion exchange, or during the preparation of a washcoat slurry, or in-situ during the synthetization step by the addition of the enhancing metal(s) into the reaction mixture. Any one of the abovementioned metals can be used in combination with any of the other methods, for example, to incorporate two or more enhancing metals into the molecular sieve.

Preferably, the enhancing metals are non-framework metals. As used herein, a "non-framework metal" is a metal that resides within the molecular sieve pores and/or on at least a portion of the molecular sieve surface, preferably as an ionic species, does not include aluminum, and does not include atoms constituting the framework of the molecular sieve.

Preferably, the presence of an enhancing metal(s) facilitates the treatment of exhaust gases, such as exhaust gas from a diesel engine, including processes such as $NO_x$ reduction, $NH_3$ oxidation, and $NO_x$ storage.

Enhancing metals include certain transition metals, such as copper (Cu), iron (Fe), manganese (Mn), nickel (Ni), molybdenum (Mo), and zinc (Zn), with copper and/or iron being preferred and copper being most preferred. Certain enhancing metals are precious metals, such as gold (Au) and silver (Ag), and also platinum group metals such as platinum (Pt), palladium (Pd), ruthenium (Ru), and rhodium (Rh). Additionally, enhancing metals can be one or more rare earth metals such as cerium (Ce), praseodymium (Pr), neodymium (Nd), europium (Eu), erbium (Er), gadolinium (Gd), ytterbium (Yb), and yttrium (Y) which can be used to improve catalytic performance, particularly when used in combination with a transition metal. (Although yttrium can be described as a transition metal, it is referred to herein as a rare earth metal due to its lanthanide-like properties.) Preferred rare earth metals include yttrium and erbium. In certain examples, STA-30 molecular sieve catalyst uses one or more transition metals in combination with one or more rare earth metals.

Preferably, transition metals are incorporated into STA-30 molecular sieves after synthesis via an ionic exchange process. Rare earth metals are preferably incorporated into STA-30 either in-situ, post synthesis, or both. For example, cerium and yttrium may be incorporated into the molecular sieve by post-synthesis ion exchange. Alternatively, yttrium may be incorporated in-situ and cerium may be incorporated by post-synthesis ion exchange. Preferred catalysts, particularly for the treatment of exhaust gas, include STA-30 having exchanged copper and exchanged yttrium, having exchanged copper and exchanged cerium, having exchanged copper, exchanged yttrium, and exchanged cerium, or having exchanged copper, exchanged cerium, and yttrium incorporated in-situ.

When two or more enhancing metals are present in STA-30 molecular sieve catalyst, each of those metals may independently be locally concentrated in different locations within a molecular sieve crystal or may have a concentration gradient within the crystal. For example, STA-30 molecular sieve catalyst may have relatively higher concentration of yttrium and/or erbium in an interior zone of the crystal relative to an exterior zone, may have relatively higher concentration of copper and/or cerium in an exterior zone of the crystal relative to an interior zone, or both. As used herein, an "interior zone" of a molecular sieve crystal means the interior 50% of the crystal by volume and "exterior zone" of a molecular sieve crystal means the exterior 50% of the crystal by volume. For example, yttrium can be present in the interior and exterior zones of STA-30 crystals in a ratio of about 60:40, about 70:30, about 80:20, or about 90:10. Erbium can be present in the interior and exterior zones of STA-30 crystals in a ratio of about 60:40, about 70:30, about 80:20, or about 90:10. Copper can be present in the exterior and interior zones of STA-30 molecular sieve crystals in a ratio of about 60:40, about 70:30, about 80:20, or about 90:10. Iron can be present in the exterior and interior zones of STA-30 molecular sieve crystals in a ratio of about 60:40, about 70:30, about 80:20, or about 90:10. Cerium can be present in the exterior and interior zones of STA-30 crystals in a ratio of about 60:40, about 70:30, about 80:20, or about 90:10.

The one or more enhancing metals are preferably present in the disordered molecular sieve material at a concentration of about 0.1 to about 10 weight percent (wt. %) based on the total weight of the molecular sieve, for example from about 0.5 wt % to about 5 wt. %, from about 0.5 to about 1 wt. %, about 1 to about 1.5 wt. %, about 1 to about 2 wt. %, from about 1 to about 5 wt. %, about 2.5 wt. % to about 3.5 wt. %, and from about 3.5 to about 5 wt. %. For embodiments which utilized two or more enhancing metals, each metal independently can be present in the abovementioned amounts.

Catalysts which utilize copper, iron, or the combination thereof, preferably have a concentration of these transition metals in STA-30 molecular sieve material of about 1 to about 5 weight percent, more preferably about 2.5 to about 4.5 weight percent based on the total weight of STA-30 molecular sieve. Catalysts which utilize copper and a rare earth metal such as yttrium, preferably have a copper concentration of about 1 to about 5 weight percent, more preferably about 2.5 to about 3.5 weight percent, and a rare earth metal concentration of about 0.05 to about 3 weight percent, based on the total weight of STA-30 molecular sieve.

Catalysts which utilize yttrium and/or erbium preferably have a concentration of these metals in STA-30 of about 0.05 to about 3 weight percent, such as about 0.1 to 1 weight percent, about 0.5 to 2 weight percent, or about 1 to 2 weight percent, based on the total weight of STA-30 molecular sieve. In certain embodiments, the yttrium and/or erbium is used to enhance the performance of a transition metal that is exchanged into the molecular sieve. Preferably, the presence of yttrium and/or erbium allows for at least a proportionate reduction in the amount of transition metal, such as copper, exchanged into STA-30 while still achieving similar catalytic performance compared to STA-30 molecular sieve having only copper exchanged into the molecular sieve at higher loadings.

The cerium concentration in the catalyst material can be from about 50 to about 550 $g/ft^3$. Other ranges of Ce are: over 100 $g/ft^3$; over 200 $g/ft^3$; over 300 $g/ft^3$; over 400 $g/ft^3$; over 500 $g/ft^3$; from about 75 to about 350 $g/ft^3$; Includes up to about 300 $g/ft^3$ and from about 100 to about 250 $g/ft^3$.

In certain embodiments, the concentration of Ce exceeds the theoretical maximum amount available for exchange on a metal promoted molecular sieve. Thus, in some embodiments, Ce is present in more than one form such as Ce ions, monomeric ceria, oligomeric ceria, and combinations thereof, provided that said oligomeric ceria is less than 5 μm, for example, It has an average crystal size of less than 1 μm, about 10 nm to about 1 μm, about 100 nm to about 1 μm, about 500 nm to about 1 µm, about 10 to about 500 nm, about 100 to about 500 nm, and about 10 to about 100 nm. As used herein, the term "monomer ceria" means $CeO_2$ as an individual molecule or moiety that is free on and/or within the molecular sieve or is weakly bound to the molecular sieve. As used herein, the term "oligomeric ceria" means nanocrystalline $CeO_2$ that is free on and/or within the molecular sieve or is weakly bound to the molecular sieve.

In certain examples, the catalyst composition is essentially free of certain catalytically active or enhancing metals or metal impurities. With reference to a catalytically active or enhancing metal, the term "essentially free" means that the material does not have an appreciable amount of the particular metal. That is, the particular metal is not present in amount that would affect the basic physical and/or chemical properties of the material, particularly with respect to the material's capacity to selectively reduce or store $NO_x$. Examples catalyst composition being essentially free of catalytically active or enhancing metals include the catalyst composition having less than 0.5 wt. %, 0.1 wt. %, 0.05 wt. % or 0.01 wt. % of the specified metal based on the total weight of the catalyst composition.

The catalyst composition can be essentially free of any rare earth metals. Alternatively, the catalyst composition may be essentially free of rare earth metals except yttrium, essentially free of rare earth metals except yttrium and erbium, or essentially free of rare earth metals except erbium.

The catalyst composition can contain noble metals, such as, Pt, Pd, Ru, Rh, Os, Ir, Ag, or Au. In other embodiments, the catalyst composition can be essentially free of any precious metals. Alternatively, the catalyst composition may be essentially free of precious metals except palladium, platinum, and rhodium, essentially free of precious metals except palladium and platinum, or essentially free of precious metals except palladium.

The catalyst composition can be essentially free of any non-framework transition metal. Alternatively, the catalyst composition may be essentially free of non-framework transition metals except copper and iron. In certain examples, the catalyst is essentially free of any non-framework transition metal except copper.

It will be understood that STA-30 molecular sieve catalysts which are characterized as being essentially free of a metal can be free of any combination of excluded metals as described herein. For example, a catalyst composition can be essentially free of any non-framework transition metal except copper and essentially free of rare earth metals except yttrium or essentially free of any non-framework transition metal except copper and essentially free of rare earth metals except erbium.

Metal exchanged STA-30 molecular sieve catalysts of the present invention are particularly applicable for heterogeneous catalytic reaction systems (i.e., solid catalyst in contact with a gas reactant). To improve contact surface area, mechanical stability, and/or fluid flow characteristics, the catalysts can be disposed on and/or within a substrate, preferably a porous substrate. In certain embodiments, a washcoat containing the catalyst is applied to an inert substrate, such as corrugated metal plate or a honeycomb cordierite brick. Alternatively, the catalyst is kneaded along with other components such as fillers, binders, and reinforcing agents, into an extrudable paste which is then extruded through a die to form a honeycomb brick. Accordingly, the present invention provides a catalyst article comprising a STA-30 catalyst described herein coated on and/or into a substrate or is formed as an extruded catalyst body.

Certain aspects of the invention provide a catalytic washcoat designed to be applied to a substrate. A washcoat comprising STA-30 molecular sieve catalyst described herein is preferably a solution, suspension, or slurry. Such washcoats can also include non-catalytic components, such as fillers, binders, stabilizers, rheology modifiers, and other additives, including one or more of alumina, silica, non-zeolite silica alumina, titania, zirconia, and ceria. These non-catalytic components are present in the catalyst composition but serve one or more non-catalytic purposes. For embodiments where the molecular sieve in the catalyst contains Ce, the corresponding washcoat may further comprise a binder containing Ce or ceria. For such embodiments, the Ce-containing particles in the binder are significantly larger than the Ce-containing particles in the catalyst.

In certain embodiments, the catalyst washcoat composition may comprise pore-forming agents such as graphite, cellulose, starch, polyacrylate, and polyethylene, and the like. These additional components do not necessarily catalyze the desired reaction, but instead improve the catalytic material's effectiveness, for example, by increasing its operating temperature range, increasing contact surface area of the catalyst, increasing adherence of the catalyst to a substrate, etc.

Two of the most common substrate designs to which catalyst may be applied are plate and honeycomb. Preferred substrates, particularly for mobile applications, include flow-through monoliths having a so-called honeycomb geometry that comprise multiple adjacent, parallel channels that are open on both ends and generally extend from the inlet face to the outlet face of the substrate and result in a high-surface area-to-volume ratio. For certain applications, the honeycomb flow-through monolith preferably has a high cell density, for example about 600 to 800 cells per square inch, and/or an average internal wall thickness of about 0.18-0.35 mm, preferably about 0.20-0.25 mm. For certain other applications, the honeycomb flow-through monolith preferably has a low cell density of about 150-600 cells per square inch, more preferably about 200-400 cells per square inch. Preferably, the honeycomb monoliths are porous. In addition to cordierite, silicon carbide, silicon nitride, ceramic, and metal, other materials that can be used for the substrate include aluminum nitride, silicon nitride, aluminum titanate, α-alumina, mullite, e.g., acicular mullite, pollucite, a thermet such as $Al_2O_sZFe$, $Al_2O_3/Ni$ or $B_4CZFe$, or composites comprising segments of any two or more thereof. Preferred materials include cordierite, silicon carbide, and alumina titanate.

Wall-flow substrates have a porosity and pore size that is gas permeable, but traps a major portion of the particulate matter, such as soot, from the gas as the gas passes through the wall. Preferred wall-flow substrates are high efficiency filters. Wall flow filters for use with the present invention preferably have an efficiency of least 70%, at least about 75%, at least about 80%, or at least about 90%. In certain embodiments, the efficiency will be from about 75 to about 99%, about 75 to about 90%, about 80 to about 90%, or about 85 to about 95%. Here, efficiency is relative to soot and other similarly sized particles and to particulate concentrations typically found in conventional diesel exhaust gas. For example, particulates in diesel exhaust can range in size from 0.05 microns to 2.5 microns. Thus, the efficiency can be based on this range or a sub-range, such as 0.1 to 0.25 microns, 0.25 to 1.25 microns, or 1.25 to 2.5 microns.

Preferred wall-flow filters have a porosity of about 30 to about 80%, for example about 40 to about 75%, about 40 to about 65%, or from about 50 to about 60%. Porosity is a measure of the percentage of void space in a porous substrate and is related to backpressure in an exhaust system: generally, the lower the porosity, the higher the backpressure.

Preferred wall-flow filters also have a pore interconnectivity volume of at least about 30%, more preferably at least about 40%. Pore interconnectivity, measured as a percentage of the substrate's total void volume, is the degree to which pores, void, and/or channels, are joined to form continuous paths through a porous substrate, i.e., from the inlet face to the outlet face. In contrast to pore interconnectivity is the sum of closed pore volume and the volume of pores that have a conduit to only one of the surfaces of the substrate.

The mean pore size of the preferred wall-flow filters is also important for filtration. Mean pore size can be determined by any acceptable means, including by mercury porosimetry. The mean pore size of the porous substrate should be of a high enough value to promote low backpressure, while providing an adequate efficiency by either the substrate per se, by promotion of a soot cake layer on the surface of the substrate, or combination of both. Preferred porous substrates have a mean pore size of about 10 to about 40 μm, for example about 20 to about 30 μm, about 10 to about 25 μm, about 10 to about 20 μm, about 20 to about 25 μm, about 10 to about 15 μm, and about 15 to about 20 μm.

Plate-type catalysts have lower pressure drops and are less susceptible to plugging and fouling than the honeycomb types, which is advantageous in high efficiency stationary applications, but plate configurations can be much larger and more expensive. A honeycomb configuration is typically smaller than a plate type, which is an advantage in mobile applications, but has higher pressure drops and plug more easily. In certain embodiments the plate substrate is constructed of metal, preferably corrugated metal.

Also provided is process for manufacturing a catalytic article. In a particular embodiment, the catalyst article is produced by a process that includes the steps of applying STA-30 catalyst composition, preferably as a washcoat, to a substrate as a layer or zone. The washcoat can be coated on a suitable substrate as a surface coating, a coating that penetrate a portion of the substrate, a coating that permeates the substrate, or some combination thereof. Either before or after STA-30 molecular sieve catalyst washcoat is applied to the substrate, one or more additional layer of another composition for treating exhaust gas can be applied to the substrate. The one or more catalyst layers on the substrate, along with STA-30 catalyst, are arranged in full or partial layers, consecutive layers, or in zones, such as a front and rear zone. As used herein, the term "consecutive" with respect to catalyst layers on a substrate means that each layer is contact with its adjacent layer(s) and that the catalyst layers as a whole are arranged one on top of another on the substrate.

The STA-30 catalyst can be disposed on the substrate as a first layer or zone and another composition, such as an oxidation catalyst, reduction catalyst, scavenging component, or $NO_x$ storage component, is disposed on the substrate as a second layer or zone.

In general, the production of an extruded solid body, such as honeycomb flow-through or wall-flow filter, containing the STA-30 catalyst involves blending STA-30 catalyst, a binder, an optional organic viscosity-enhancing compound into an homogeneous paste which is then added to a binder/matrix component or a precursor thereof and optionally one or more of stabilized ceria, and inorganic fibers. The blend is compacted in a mixing or kneading apparatus or an extruder. The mixtures have organic additives such as binders, pore formers, plasticizers, surfactants, lubricants, dispersants as processing aids to enhance wetting and therefore produce a uniform batch. The resulting plastic material is then molded, in particular, using an extrusion press or an extruder including an extrusion die, and the resulting moldings are dried and calcined. The organic additives are "burnt out" during calcinations of the extruded solid body. A STA-30 catalyst may also be washcoated or otherwise applied to the extruded solid body as one or more sub-layers that reside on the surface or penetrate wholly or partly into the extruded solid body. Preferably, STA-30 molecular sieve catalyst is dispersed throughout, and preferably evenly throughout, the entire extruded catalyst body.

Where any of the above extruded solid bodies are made into a wall-flow filter, the porosity of the wall-flow filter can be from 30-80%, such as from 40-70%. Porosity and pore volume and pore radius can be measured e.g. using mercury intrusion porosimetry.

The STA-30 molecular sieve catalyst described herein can promote the reaction of a reductant, preferably ammonia, with nitrogen oxides to selectively form elemental nitrogen ($N_2$) and water ($H_2O$). Thus, in one embodiment, the catalyst can be formulated to favor the reduction of nitrogen oxides with a reductant (i.e., an SCR catalyst). Examples of such reductants include hydrocarbons (e.g., C3-C6 hydrocarbons) and nitrogenous reductants such as ammonia and ammonia hydrazine or any suitable ammonia precursor, such as urea (($NH_2$)$_2$CO), ammonium carbonate, ammonium carbamate, ammonium hydrogen carbonate or ammonium formate. Preferably, the catalyst has a low $N_2O$ selectivity. $N_2O$ selectivity is defined as the moles $N_2O$ formed divided by the moles of $NO_x$ ($NO_x$ defined as NO and $NO_2$) converted. Lower $N_2O$ selectivity is desired because of the need to reduce $N_2O$ formation.

The STA-30 catalyst described herein can also promote the oxidation of ammonia. Thus, in another embodiment, the catalyst can be formulated to favor the oxidation of ammonia with oxygen, particularly at concentrations of ammonia typically encountered downstream of an SCR catalyst (e.g., ammonia oxidation (AMOX) catalyst, such as an ammonia slip catalyst (ASC)). In certain embodiments, STA-30 molecular sieve catalyst is disposed as a top layer over an oxidative under-layer, wherein the under-layer comprises a platinum group metal (PGM) catalyst or a non-PGM catalyst. Preferably, the catalyst component in the underlayer is disposed on a high surface area support, including but not limited to alumina.

In yet another embodiment, an SCR and AMOX operations are performed in series, wherein both processes utilize a catalyst comprising the STA-30 catalyst described herein, and wherein the SCR process occurs upstream of the AMOX process. For example, an SCR formulation of the catalyst can be disposed on the inlet side of a filter and an AMOX formulation of the catalyst can be disposed on the outlet side of the filter.

Accordingly, provided is a method for the reduction of $NO_x$ compounds and/or oxidation of $NH_3$ in a gas, which comprises contacting the gas with a catalyst composition described herein for the catalytic reduction of $NO_x$ compounds for a time sufficient to reduce the level of $NO_x$ compounds and/or $NH_3$ in the gas. In certain embodiments, provided is a catalyst article having an ammonia slip catalyst disposed downstream of a selective catalytic reduction (SCR) catalyst. In such embodiments, the ammonia slip catalyst oxidizes at least a portion of any nitrogenous reductant that is not consumed by the selective catalytic reduction process. For example, in certain embodiments, the ammonia slip catalyst is disposed on the outlet side of a wall flow filter and an SCR catalyst is disposed on the upstream side of a filter. In certain other embodiments, the ammonia slip catalyst is disposed on the downstream end of a flow-through substrate and an SCR catalyst is disposed on the upstream end of the flow-through substrate. In other embodiments, the ammonia slip catalyst and SCR catalyst are disposed on separate bricks within the exhaust system. These separate bricks can be adjacent to, and in contact with, each other or separated by a specific distance, provided that they are in fluid communication with each other and provided that the SCR catalyst brick is disposed upstream of the ammonia slip catalyst brick.

The SCR and/or AMOX process is preferably performed at a temperature of at least 150° C., for example from about 150° C. to about 750° C., from about 175 to about 550° C., from about 175 to about 400° C., from about 450 to about 900° C., and more preferably about 450 to about 750° C., about 450 to about to 650° C., or about 450 to about 550° C. Utilizing temperatures greater than 450° C. is particularly useful for treating exhaust gases from a heavy and light duty diesel engine that is equipped with an exhaust system comprising (optionally catalyzed) diesel particulate filters which are regenerated actively, e.g., by injecting hydrocarbon into the exhaust system upstream of the filter, wherein the molecular sieve catalyst for use in the present invention is located downstream of the filter.

Additionally, methods of the present invention may comprise one or more of the following steps: (a) accumulating and/or combusting soot that is in contact with the inlet of a catalytic filter; (b) introducing a nitrogenous reducing agent into the exhaust gas stream prior to contacting the catalytic filter, preferably with no intervening catalytic steps involving the treatment of $NO_x$ and the reductant; (c) generating $NH_3$ over a $NO_x$ adsorber catalyst or lean $NO_x$ trap, and preferably using such $NH_3$ as a reductant in a downstream SCR reaction; (d) contacting the exhaust gas stream with a DOC to oxidize hydrocarbon based soluble organic fraction (SOF) and/or carbon monoxide into $CO_2$, and/or oxidize NO into $NO_2$, which in turn, may be used to oxidize particulate matter in particulate filter; and/or reduce the particulate matter (PM) in the exhaust gas; (e) contacting the exhaust gas with one or more flow-through SCR catalyst device(s) in the presence of a reducing agent to reduce the $NO_x$ concentration in the exhaust gas; and (f) contacting the exhaust gas with an ammonia slip catalyst, preferably downstream of the SCR catalyst to oxidize most, if not all, of the ammonia prior to emitting the exhaust gas into the atmosphere or passing the exhaust gas through a recirculation loop prior to exhaust gas entering/re-entering the engine.

Another aspect of the present invention is directed to a method for treating an exhaust gas comprising contacting a combustion exhaust gas containing $NO_x$ with a passive $NO_x$ absorber comprising the molecular sieve or catalyst as described above.

Another aspect of the present invention is directed to a method of converting methanol to an olefin (MTO) comprising contacting methanol with the molecular sieve or catalyst as described above.

In certain aspects, the invention is a system for treating exhaust gas generated by combustion process, such as from an internal combustion engine (whether mobile or stationary), a gas turbine, coal or oil fired power plants, and the like. Such systems include a catalytic article comprising the STA-30 catalyst described herein and at least one additional component for treating the exhaust gas, wherein the catalytic article and at least one additional component are designed to function as a coherent unit. The system can comprise a catalytic article comprising a STA-30 catalyst described herein, a conduit for directing a flowing exhaust gas, a source of nitrogenous reductant disposed upstream of the catalytic article. The system can include a controller for the metering the nitrogenous reductant into the flowing exhaust gas only when it is determined that the molecular sieve catalyst is capable of catalyzing $NO_x$ reduction at or above a desired efficiency, such as at above 100° C., above 150° C. or above 175° C. The metering of the nitrogenous reductant can be arranged such that 60% to 200% of theoretical ammonia is present in exhaust gas entering the SCR catalyst calculated at 1:1 $NH_3/NO$ and 4:3 $NH_3/NO_2$.

In another embodiment, the system comprises an oxidation catalyst (e.g., a diesel oxidation catalyst (DOC)) for oxidizing nitrogen monoxide in the exhaust gas to nitrogen dioxide can be located upstream of a point of metering the nitrogenous reductant into the exhaust gas. In one embodiment, the oxidation catalyst is adapted to yield a gas stream entering the SCR zeolite catalyst having a ratio of NO to $NO_2$ of from about 4:1 to about 1:3 by volume, e.g., at an exhaust gas temperature at oxidation catalyst inlet of 250° C. to 450° C. The oxidation catalyst can include at least one platinum group metal (or some combination of these), such as platinum, palladium, or rhodium, coated on a flow-through monolith substrate. In one embodiment, the at least one platinum group metal is platinum, palladium or a combination of both platinum and palladium. The platinum group metal can be supported on a high surface area washcoat component such as alumina, a molecular sieve such as an aluminosilicate molecular sieve, silica, non-zeolite silica alumina, ceria, zirconia, titania or a mixed or composite oxide containing both ceria and zirconia.

In a further embodiment, a suitable filter substrate is located between the oxidation catalyst and the SCR catalyst. Filter substrates can be selected from any of those mentioned above, e.g., wall flow filters. Where the filter is catalyzed, e.g., with an oxidation catalyst of the kind discussed above, preferably the point of metering nitrogenous reductant is located between the filter and the molecular sieve catalyst. Alternatively, if the filter is un-catalyzed, the means for metering nitrogenous reductant can be located between the oxidation catalyst and the filter.

EXAMPLES

Some of the SDAs used in the examples below have been prepared in-house using the following procedures.

1,7-(1,4-diazabicyclo[2.2.2]octane)heptyl dibromide: 23.1 g (0.21 mol) 1,4-diazabicyclo[2.2.2]octane were dissolved in 100 mL ethanol and heated up to 50° C. under stirring. Another solution was prepared by mixing 10.3 g (0.04 mol) 1,7-dibromoheptane and 50 mL ethanol. This solution was added dropwise into the first one. The reaction mixture was refluxed for 24 h. The ethanol was removed by the rotary evaporator and the product was washed using cold diethyl ether, acetonitrile, and acetone and dried overnight. A white solid (yield 83%) was obtained and characterised by NMR.

1,9-(1,4-diazabicyclo[2.2.2]octane)nonyl dibromide: 14.6 g (0.13 mol) 1,4-diazabicyclo[2.2.2]octane were dissolved in 50 mL ethanol and heated up to 50° C. under stirring. Another solution was prepared by mixing 5.7 g (0.02 mol) 1,9-dibromononane and 70 mL ethanol. This solution was added dropwise into the first one. The reaction mixture was refluxed for 24 hours. The ethanol was removed by the rotary evaporator and the product was washed using cold diethyl ether, acetonitrile, and acetone and dried overnight. A white solid (yield 80%) was obtained and characterised by NMR.

1,10-(1,4-diazabicyclo[2.2.2]octane)decyl dibromide: 14.6 g (0.13 mol) 1,4-diazabicyclo[2.2.2]octane were dissolved in 50 mL ethanol and heated up to 50° C. under stirring. Another solution was prepared by mixing 7.4 g (0.02 mol) 1,10-dibromodecane and 70 mL ethanol. This solution was added dropwise into the first one. The reaction mixture was refluxed for 24 hours. The ethanol was removed by the rotary evaporator and the product was washed using cold diethyl ether, acetonitrile, and acetone and dried overnight. A white solid (yield 78%) was obtained and characterised by NMR.

Method of Characterisation:

The XRD data was collected in Bragg-Brentano geometry in the 2θ range 5-50°, via a primary monochromator, at 30 kV and 10 mA on a Bruker D2 diffractometer equipped with a LynxEye detector (using Cu Kα1 X-radiation, λ=1.54059 Å, via a primary monochromator, step size 0.02°, time per step of 33 s). The sample was rotated during the data collection to minimise preferred orientation. Elemental compositions of materials discussed in this paper were determined using energy dispersive X-Ray spectroscopy (EDS) or X-ray fluorescence spectroscopy (XRF). EDX spectra were collected on a Jeol JSM-5600 instrument equipped with an Oxford Inca EDX system for compositional analysis. XRF spectra were collected on Bruker S8 WDXRF (wavelength-dispersive X-ray fluorescence) spectrometer. Ar adsorption isotherms were measured at 87 K using a Micromeritics 3-Flex apparatus. Prior to measurement the samples were heated under vacuum at 623 K for 16 h to remove physisorbed water.

The following examples are intended to be non-limiting.

Example 1

Figure 2:
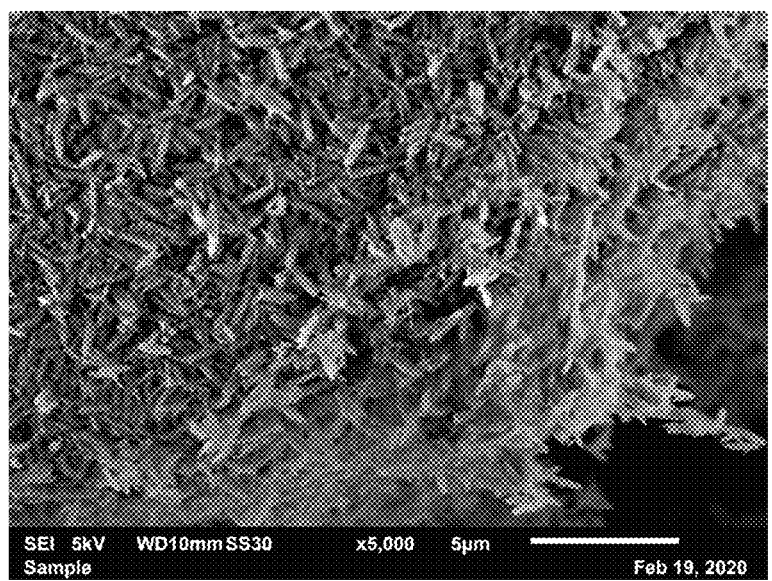
FIG. 2 shows scanning electron micrograph (SEM) of as-made STA-30 from Example 1.

0.79 g of aluminium hydroxide (76.5% min, Alfa Aesar) was dissolved in 21.72 g of tetrapropylammonium hydroxide solution (40% aq. sol., SACHEM). 16.23 g of Ludox HS-40 (Sigma Aldrich; colloidal silica, 40 wt. % suspension in $H_2O$) was then added to the previous mixture. After stirring for 1.5 hours, the solution was then transferred into a Teflon-lined stainless-steel autoclave and aged for 20 hours at 95° C. On the following day, 6.84 g of 1,8-(1,4-diazabicyclo[2.2.2]octane)octyl dibromide (Alfa Aesar) and 0.49 g of potassium hydroxide (85% purity, Alfa Aesar) were dissolved in 24.3 mL of deionised $H_2O$. This mixture was then added dropwise to the aged solution. The gel was allowed to stir for a couple of hours before transferring it into a Teflon-lined stainless-steel autoclave. The mixture was heated at 130° C. for 5 days, while rotating the autoclave at 60 rpm. The product was then recovered by centrifugation, washed with water and dried. The product was analysed by powder XRD and SEM. The comparison between the as synthesised product and the simulated pattern for an ideal SWY framework structure, in FIG. 1 confirms the phase purity of STA-30. An SEM image of the product is shown in FIG. 2. Analysis by X-ray fluorescence spectroscopy (XRF) showed the product to have a silica-to-alumina ratio (SAR) of 14.

Example 2

Figure 3:
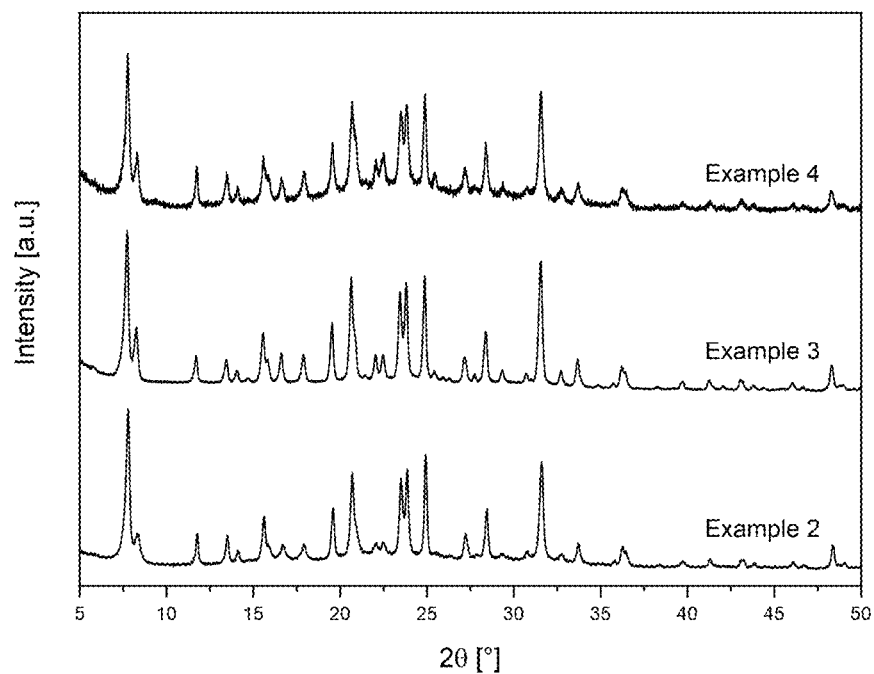
FIG. 3 shows powder X-ray diffraction (XRD) patterns of as-made STA-30 samples of Example 2, Example 3, and Example 4.

0.84 g of aluminium isopropoxide (98% purity, Acros Organics) was dissolved in 8.32 g of tetraethylammonium hydroxide solution (35% aq. sol., Sigma Aldrich). 6.19 g of Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 2.56 g of 1,8-(1,4-diazabicyclo[2.2.2]octane)octyl dibromide (Alfa Aesar) and 0.28 g of potassium hydroxide (Fisher Scientific) were dissolved in 6.9 mL of deionised $H_2O$. This mixture was then added dropwise to the aged solution. The gel was allowed to stir for a couple of hours before transferring it into a Teflon-lined stainless-steel autoclave. The mixture was heated at 130° C. for 5 days, while rotating the autoclave at 60 rpm. The product was treated as described in Example 1, then analysed by powder XRD (FIG. 3). The product comprised phase-pure zeolite STA-30. Analysis by Energy-dispersive X-ray Spectroscopy (EDS) showed the product to have a silica-to-alumina ratio (SAR) of 12.5.

Example 3

0.73 g of aluminium isopropoxide (98% purity, Acros Organics) was dissolved in 9.17 g of tetrabutylammonium hydroxide solution (40% aq. sol., Avocado). 5.36 g of Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 2.22 g of 1,8-(1,4-diazabicyclo[2.2.2]octane)octyl dibromide (Alfa Aesar) and 0.24 g of potassium hydroxide (Fisher Scientific) were dissolved in 4.3 mL of deionised $H_2O$. This mixture was then added dropwise to the aged solution. The gel was allowed to stir for a couple of hours before transferring it into a Teflon-lined stainless-steel autoclave. The mixture was heated at 130° C. for 5 days, while rotating the autoclave at 60 rpm. The product was treated as described in Example 1, then analysed by powder XRD (FIG. 3). The product comprised phase-pure zeolite STA-30. Analysis by EDS showed the product to have a silica-to-alumina ratio (SAR) of 12.

Example 4

0.74 g of aluminium isopropoxide (98% purity, Acros Organics) was dissolved in 8.31 g of tetrapropylammonium hydroxide solution (40% aq. sol., SACHEM). 6.26 g of Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 2.53 g of 1,7-(1,4-diazabicyclo[2.2.2]octane)heptyl dibromide (prepared in-house) and 0.20 g of potassium hydroxide (Fisher Scientific) were dissolved in 6.4 mL of deionised $H_2O$. This mixture was then added dropwise to the aged solution. The gel was allowed to stir for a couple of hours before transferring it into a Teflon-lined stainless-steel autoclave. The mixture was heated at 130° C. for 5 days, while rotating the autoclave at 60 rpm. The product was treated as described in Example 1, then analysed by powder XRD (FIG. 3). The product comprised phase-pure zeolite STA-30. Analysis by EDS showed the product to have a silica-to-alumina ratio (SAR) of 10.5.

Example 5

The as-made zeolite from Example 1 was activated by calcining in air. The solid was heated to 110° C. at 2° C./min then heated to 450° C. at 5° C./min and held at 450° C. for 16 hours. Finally, the material was heated to 550° C. at 5°

C./min at held at 550° C. for 16 hours. Once the solid had cooled to room temperature, it was ion-exchanged with a 1 M solution of ammonium chloride using 100 mL of solution per gram of calcined zeolite. The ion-exchange was carried out with stirring at room temperature for 1 hour. The solution and the zeolite were then separated, and the sample was exchanged for a further hour with a fresh batch of 1M ammonium chloride solution. Ultimately, the sample was filtered and washed. The resulting $NH_4$-form zeolite was converted to the H-form by calcining, in air, by heating to 150° C. at 2° C./min and holding at 150° C. for 10 hours followed by heating to 450° C. at 5° C./min with a final hold at 450° C. for 16 hours. XRD pattern of active material is shown in FIG. 1. The material exhibits a micropore volume of 0.28 cm$^3$/g and BET area of 755 m$^2$/g determined by Ar adsorption Isotherm.

Example 6: Selective Catalytic Reduction (SCR) Performance

STA-30 zeolite synthesized according to Example 1 and activated following the procedure described in Example 5 was impregnated with metal using the required amount of copper (II) acetate dissolved in de-mineralized water. The metal impregnated zeolite was dried overnight at 80° C. and then calcined in air at 550° C. for 4 hours. Copper was added to the zeolite to achieve a STA-30 having 3.3 wt. % copper based on the total weight of the zeolite. A reference sample of BEA (SAR-28) having 3.3 wt. % copper was prepared following the same method described above.

Pelletized samples of the copper STA-30 and BEA reference were placed in a test rig. To assess the zeolite's SCR performance over a range of temperatures, the zeolite was subjected to a flow of simulated diesel engine exhaust gas having the following properties: 500 ppm $NH_3$, 500 ppm NO, 0 ppm $NO_2$, SV=90 K h$^{-1}$. The sample was heated from room temperature to 150° C. under the above-mentioned gas mixture except for $NH_3$. At 150° C., $NH_3$ was added into the gas mixture and the sample was held under these conditions for 30 minutes. The temperature was then increased from 150° C. to 500° C. at a rate of 5° C./minute. The downstream gas treated by the zeolite was monitored to determine $NO_x$ conversion and $N_2O$ selectivity.

Figure 4:
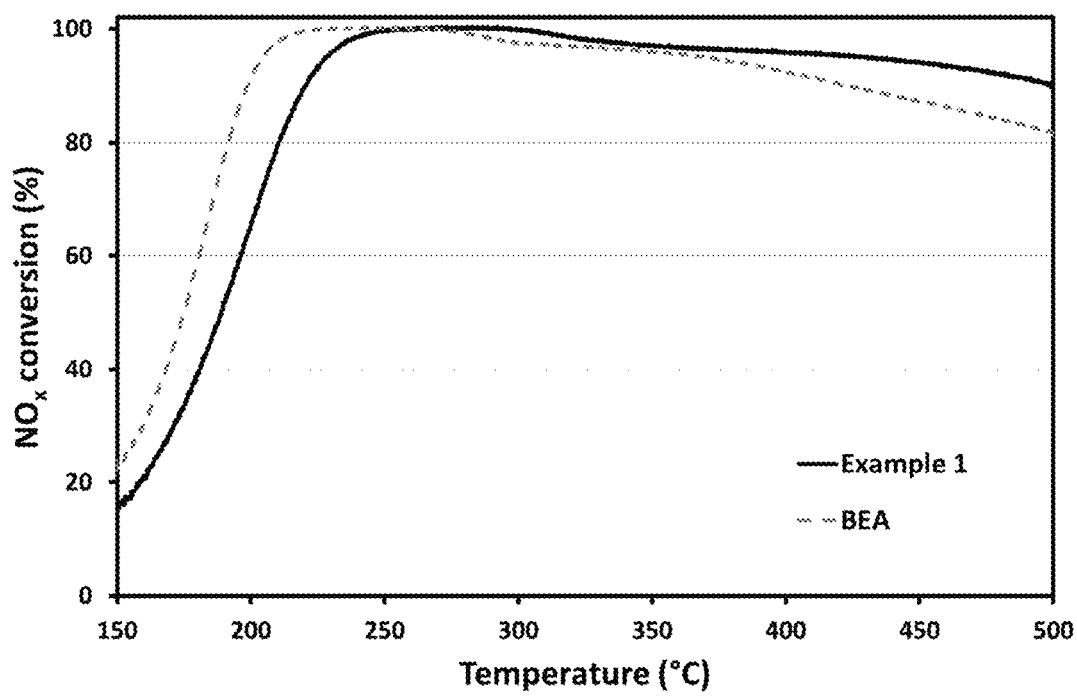
FIG. 4 shows $NO_x$ conversion for the fresh copper STA-30 (H-form Example 1) compared to that of pure copper BEA zeolite for the Selective Catalytic Reduction (SCR) of $NO_x$.

$NO_x$ conversion activity profile results are depicted in FIG. 4. It has been found that a fresh sample of Example 1 demonstrated $NO_x$ conversion levels of 1%-15% higher than the benchmark BEA.Cu in the temperatures range of 340° C.-550° C. Therefore, it has been demonstrated that the Example according to the present invention exhibits significant advantages in $NO_x$ conversion when utilized in the optimal operating temperature range.

Figure 5:
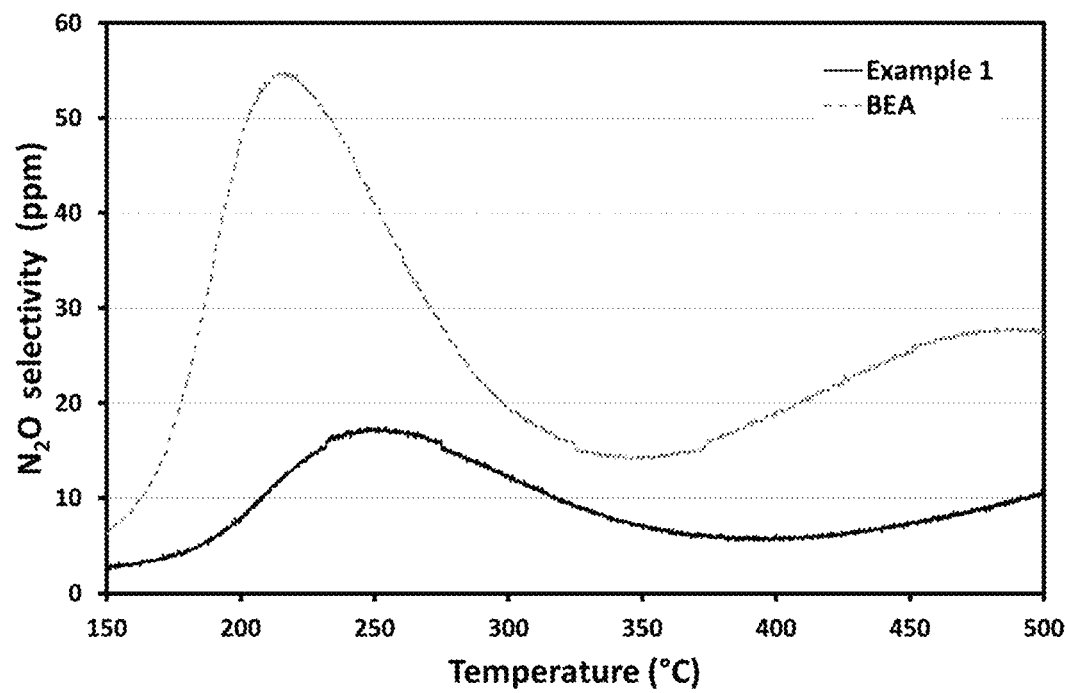
FIG. 5 shows $N_2O$ selectivity for the fresh copper STA-30 (H-form Example 1) compared to that of pure copper BEA zeolite for the Selective Catalytic Reduction (SCR) of $NO_x$.

The concentration of $N_2O$ in gas passing through fresh catalysts over temperatures from 150° C. to 500° C. are given in FIG. 5. Gas flowing into the apparatus contained 500 ppm $NO_x$ as NO-only. The levels of $N_2O$ produced by Example 1 were all significantly lower (~18 ppm peak value) than that of BEA (peak values of ~55 ppm and 28 ppm) over the entire temperature range. Thus, the Example according to the present invention exhibits significant advantages in $N_2O$ production over BEA fresh.

Example 7

Figure 6:
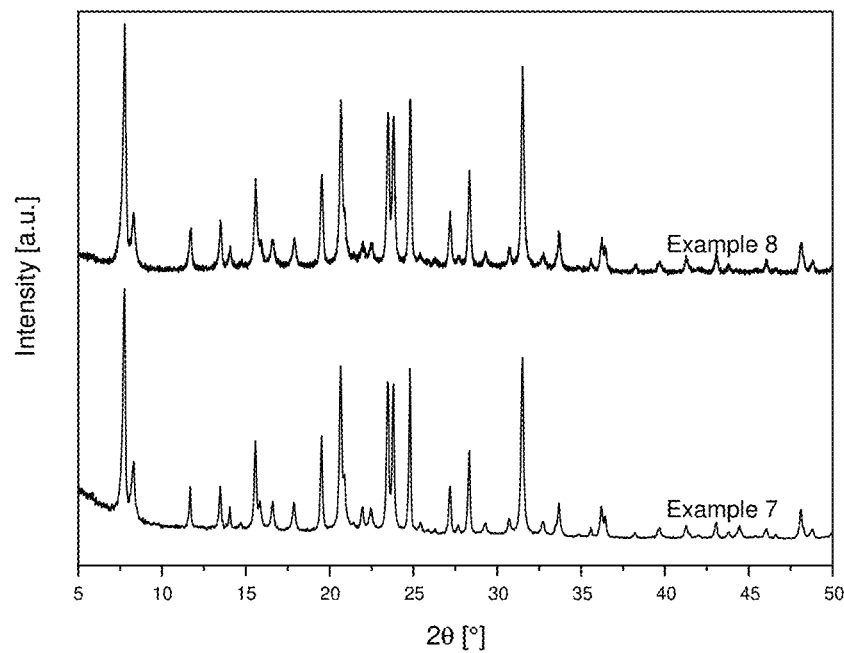
FIG. 6 shows powder X-ray diffraction (XRD) patterns of as-made STA-30 samples of Example 7 and Example 8.

0.75 g of aluminium isopropoxide (98% purity, Acros Organics) was dissolved in 8.32 g of tetrapropylammonium hydroxide solution (40% aq. sol., SACHEM). 6.19 g of Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 2.70 g of 1,9-(1,4-diazabicyclo[2.2.2]octane)nonyl dibromide (prepared in-house) and 0.20 g of potassium hydroxide (85% purity, Fisher Scientific) were dissolved in 6.4 mL of deionised $H_2O$. This mixture was then added dropwise to the aged solution. The gel was allowed to stir for a couple of hours before transferring it into a Teflon-lined stainless-steel autoclave. The mixture was heated at 130° C. for 5 days, while rotating the autoclave at 60 rpm. The product was treated as described in Example 1, then analysed by powder XRD (FIG. 6). The product comprised phase-pure zeolite STA-30. Analysis by EDS showed the product to have a silica-to-alumina ratio (SAR) of 12.2.

Example 8

0.75 g of aluminium isopropoxide (98% purity, Acros Organics) was dissolved in 8.32 g of tetrapropylammonium hydroxide solution (40% aq. sol., SACHEM). 6.22 g of Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 2.77 g of 1,10-(1,4-diazabicyclo[2.2.2]octane)decyl dibromide (prepared in-house) and 0.20 g of potassium hydroxide (85% purity, Fisher Scientific) were dissolved in 6.4 mL of deionised $H_2O$. This mixture was then added dropwise to the aged solution. The gel was allowed to stir for a couple of hours before transferring it into a Teflon-lined stainless-steel autoclave. The mixture was heated at 130° C. for 5 days, while rotating the autoclave at 60 rpm. The product was treated as described in Example 1, then analysed by powder XRD (FIG. 6). The product comprised phase-pure zeolite STA-30. Analysis by EDS showed the product to have a silica-to-alumina ratio (SAR) of 11.8.

Example 9

Figure 7:
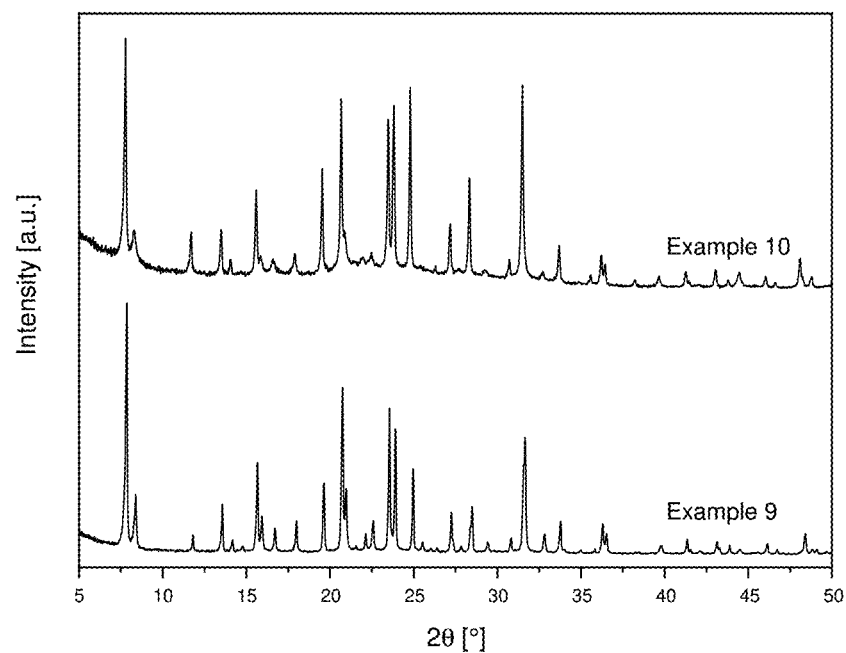
FIG. 7 shows powder X-ray diffraction (XRD) patterns of as-made STA-30 samples of Example 9 and Example 10.

0.63 g of aluminium isopropoxide (98% purity, Acros Organics) was dissolved in 8.31 g of tetrapropylammonium hydroxide solution (40% aq. sol., SACHEM). 6.19 g of Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 1.16 g of 1,4-diazabicyclo[2.2.2]octane (Sigma Aldrich) and 0.28 g of potassium hydroxide (85% purity, Fisher Scientific) were dissolved in 6.4 mL of deionised $H_2O$. This mixture was then added dropwise to the aged solution. Additionally, 1.39 g of 1,8-dibromooctane (Lancaster Synthesis) were added. The gel was allowed to stir for a couple of hours before transferring it into a Teflon-lined stainless-steel autoclave. The mixture was heated at 135° C. for 5 days, while rotating the autoclave at 60 rpm. The product was treated as described in Example 1, then analysed by powder XRD (FIG. 7). The product comprised phase-pure zeolite STA-30. Analysis by EDS showed the product to have a silica-to-alumina ratio (SAR) of 13.1.

Example 10

0.74 g of aluminium isopropoxide (98% purity, Acros Organics) was dissolved in 8.31 g of tetrapropylammonium hydroxide solution (40% aq. sol., SACHEM). 6.18 g of Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 1.35 g of 1,4-diazabicyclo [2.2.2]octane (Sigma Aldrich) and 0.21 g of potassium hydroxide (85% purity, Fisher Scientific) were dissolved in 6.4 mL of deionised $H_2O$. This mixture was then added dropwise to the aged solution. Additionally, 1.71 g of 1,10-dibromodecane (Sigma Aldrich) were added. The gel was allowed to stir for a couple of hours before transferring it into a Teflon-lined stainless-steel autoclave. The mixture was heated at 130° C. for 5 days, while rotating the autoclave at 60 rpm. The product was treated as described in Example 1, then analysed by powder XRD (FIG. 7). The product comprised phase-pure zeolite STA-30. Analysis by EDS showed the product to have a silica-to-alumina ratio (SAR) of 10.9.

Example 11

Figure 8:
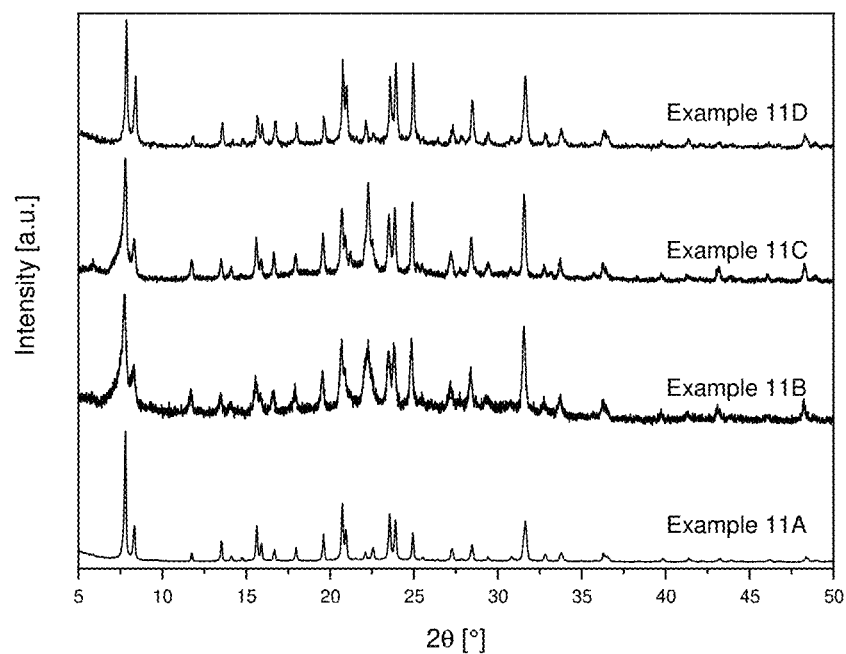
FIG. 8 shows powder X-ray diffraction (XRD) patterns of as-made STA-30 samples of Example 11.

The amounts of all reagents can be found in Table 3. Aluminium isopropoxide (98% purity, Acros Organics, Table 3, Al—I) or aluminium hydroxide (76.5% min, Alfa Aesar, Table 3, Al—H) was dissolved in tetrapropylammonium hydroxide solution (40% aq. sol., SACHEM). Ludox HS-40 (Sigma Aldrich) was then added to the previous mixture. After stirring for 1.5 hours, the solution was then transferred into a Teflon-lined stainless-steel autoclave and aged for 20 hours at 95° C. On the following day, 1,8-(1, 4-diazabicyclo[2.2.2]octane)octyl dibromide (Alfa Aesar, SDA-1 in Table 3), 1,8-(1,4-diazabicyclo[2.2.2]octane)octyl dihydroxide (20% aq. sol., Alfa Aesar, SDA-2 in Table 3), potassium hydroxide (85% purity, Fisher Scientific) were dissolved in deionised $H_2O$. One of the following was also added to the gel in some instances: strontium nitrate (Alfa Aesar), lithium nitrate (Sigma Aldrich) or caesium hydroxide (50% aq. sol., Alfa Aesar). This mixture was then added dropwise to the aged solution. The gel was allowed to stir for a couple of hours before transferring it into a Teflon-lined stainless-steel autoclave. The mixture was heated at 130-140° C. for 5 days, while rotating the autoclave at 60 rpm. The products were treated as described in Example 1, then analysed by powder XRD (FIG. 8). Compositional analysis was carried out by EDS or XRF, and particle size and morphology of the products' crystallites were determined by SEM. The specific details for each product are presented in Table 4.

Example 12

Figure 10:
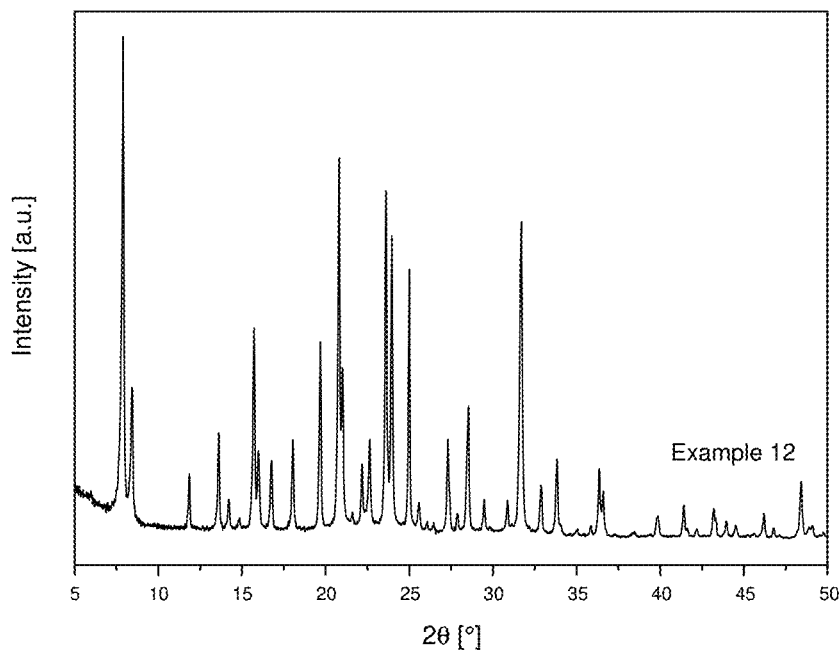
FIG. 10 shows a powder X-ray diffraction (XRD) pattern of STA-30 as-prepared in Example 12.

0.65 g of aluminium isopropoxide (98% purity, Acros Organics) was dissolved in 15.10 g of 1,8-(1,4-diazabicyclo [2.2.2]octane)octyl dihydroxide (20% aq. sol., Alfa Aesar). 6.22 g of Ludox HS-40 (Sigma Aldrich) was then added to the previous mixture and the mixture was left stirring for 1.5 hours. Then, 2.01 g of 1,8-(1,4-diazabicyclo[2.2.2]octane) octyl dibromide (Alfa Aesar) and 0.19 g of potassium hydroxide (Fisher Scientific) were added to the solution. The gel was allowed to stir for a couple of hours before transferring it into a Teflon-lined stainless-steel autoclave. The mixture was heated at 135° C. for 5 days, while rotating the autoclave at 60 rpm. The product was treated as described in Example 1, then analysed by powder XRD (FIG. 10). The product comprised phase-pure zeolite STA-30. Analysis by EDS showed the product to have a silica-to-alumina ratio (SAR) of 12.9.

Example 13

Figure 11:
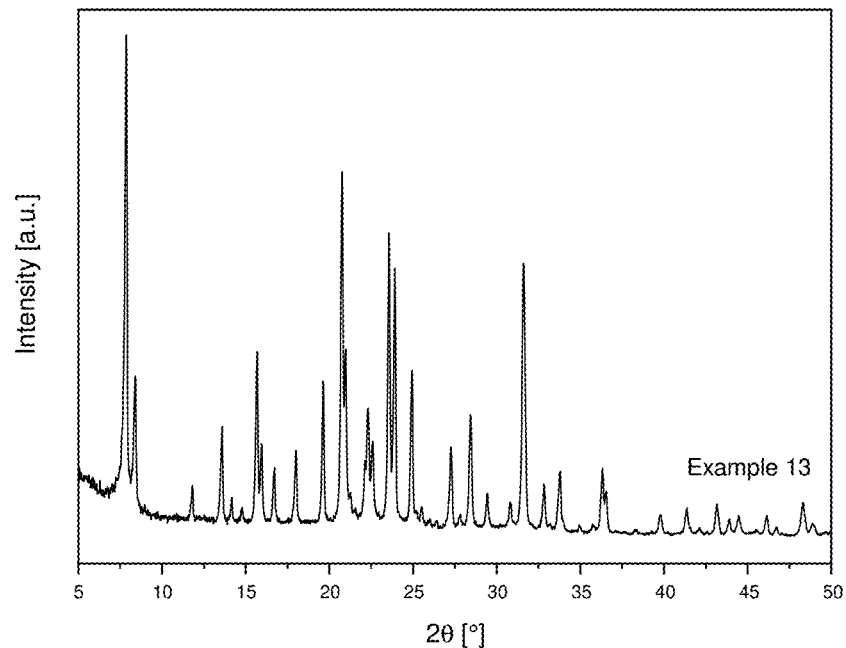
FIG. 11 shows a powder X-ray diffraction (XRD) pattern of STA-30 as-prepared in Example 13.
Figure 12:
FIG. 12 shows scanning electron micrograph (SEM) of as-made STA-30 from Example 13.

2.45 g of CBV-712 (Zeolyst, SAR-12) was dissolved in 16.59 g of 1,8-(1,4-diazabicyclo[2.2.2]octane)octyl dihydroxide (20% aq. sol., Alfa Aesar). 1.73 g of Ludox HS-40 (Sigma Aldrich) was then added to the previous mixture and the mixture was left stirring for 1.5 hours. Then, 1.60 g of 1,8-(1,4-diazabicyclo[2.2.2]octane)octyl dibromide (Alfa Aesar) and 0.50 g of potassium hydroxide (Fisher Scientific) were dissolved in 1.0 mL of deionised $H_2O$. This mixture was then added dropwise to the solution. The gel was allowed to stir for a couple of hours and then 0.15 g of STA-30 was added. The mixture was transferred into a Teflon-lined stainless-steel autoclave and it was heated at 160° C. for 2 days, while rotating the autoclave at 60 rpm. The product was treated as described in Example 1, then analysed by powder XRD (FIG. 11). The product comprised phase-pure zeolite STA-30. An SEM image of the product is shown in FIG. 12. EDS showed the product to have a silica-to-alumina ratio (SAR) of 12.6.

The invention claimed is:

1. A molecular sieve comprising a SWY type framework (STA-30), wherein the molecular sieve has a molar relationship: $Al_2O_3:(n)SiO_2$, wherein n represents the molar ratio of $SiO_2$ to $Al_2O_3$.

TABLE 3

Reaction Mixture Compositions in Example 11

| | Aluminium source and amount (g) | | Ludox HS-40 amount (g) | KOH (g) | TPAOH solution (g) | Other alkali or alkaline earth metal cations (g) | | SDA-1 (g) | SDA-2 (g) | $H_2O$ (mL) |
|---|---|---|---|---|---|---|---|---|---|---|
| Example 11A | Al—H | 0.79 | 16.23 | 0.49 | 21.72 | n/a | n/a | 6.84 | n/a | 24.3 |
| Example 11B | Al—I | 0.76 | 6.20 | 0.14 | 8.31 | $Sr(NO_3)_2$ | 0.53 | 1.96 | 2.14 | 4.7 |
| Example 11C | Al—I | 0.75 | 6.18 | 0.14 | 8.31 | $LiNO_3$ | 0.17 | 1.96 | 2.34 | 4.4 |
| Example 11D | Al—I | 2.76 | 16.34 | 0.43 | 21.86 | CsOH | 0.65 | 6.88 | n/a | 16.8 |

TABLE 4

SAR, particle size and morphology of crystallites from Example 11

Figure 9:
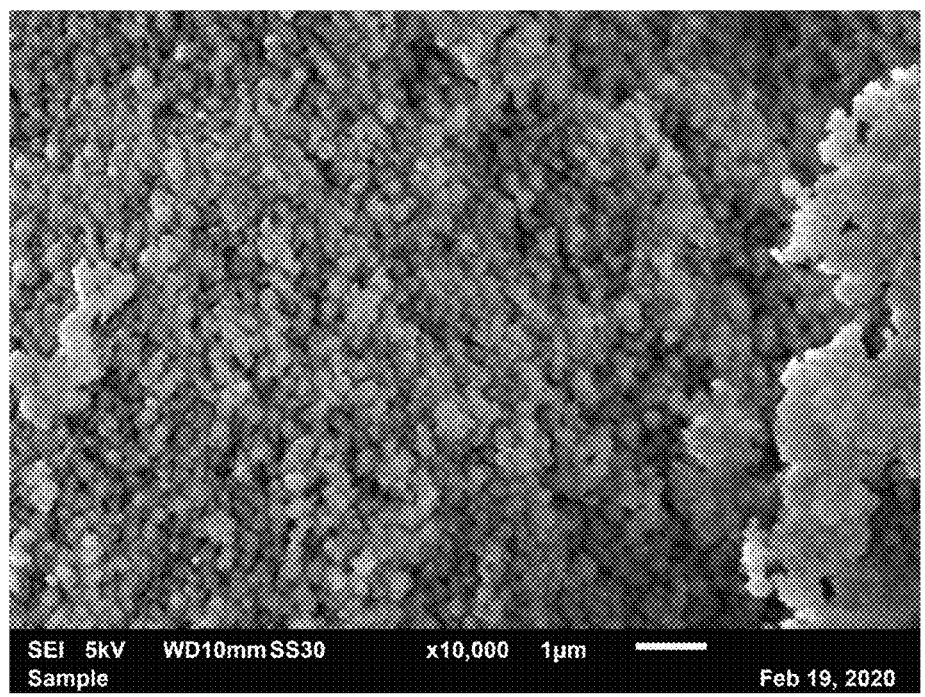
FIG. 9 shows scanning electron micrograph (SEM) of as-made STA-30 from Example 11D.

| | SAR | Method | Particle size | Particle morphology |
|---|---|---|---|---|
| Example 11A | 14.2 | XRF | 0.5-1.4 μm | rice grain |
| Example 11B | 11.5 | EDS | 0.5-1.1 μm | rice grain |
| Example 11C | 13.1 | EDS | 0.4-0.9 μm | rice grain |
| Example 11D | 10.8 | XRF | 0.2-0.4 μm | spherical (FIG. 9) |

2. The molecular sieve of claim 1, wherein n is from about 5 to about 50.

3. The molecular sieve of claim 1, wherein the molecular sieve has at least 95 mol. % of SWY framework.

4. The molecular sieve of claim 1, wherein the molecular sieve is substantially free of phosphorus within the framework.

5. The molecular sieve of claim 1, where the molecular sieve further comprises at least one extra-framework transition metal selected from the group consisting of Ag, Ce, Co, Cr, Cu, Fe, Ga, In, Ir, Mn, Mo, Ni, Pd, Pt, Re, Rh, Ru, Sn and Zn.

6. The molecular sieve of claim 1, where the molecular sieve is calcined.

7. The molecular sieve of claim 1, where the molecular sieve further comprises one or more SDAs.

8. The molecular sieve of claim 7, where the SDA comprises one or more 1,4-diazabicyclo[2.2.2]octane and 1-azabicyclo[2.2.2]octane dications derivates.

9. A catalyst comprising an STA-30 molecular sieve of claim 1.

10. The catalyst of claim 9, wherein the molecular sieve comprises about 0.1 to about 10 weight percent of a transition metal or noble metal.

11. The catalyst of claim 10, wherein the transition metal comprises copper and the molecular sieve comprises about 1 to about 5 weight percent ionic copper.

12. The catalyst of claim 10, wherein the noble metal is selected from the group consisting of Pt, Pd, Ru, Rh, Os, Ir, Ag, and Au.

13. A method for synthesizing an aluminosilicate molecular sieve comprising a SWY type framework (STA-30), the method comprising:
(1) forming heating a reaction mixture comprising: (a) at least one source of silicon oxide; (b) at least one source of aluminum oxide; (c) a source of alkali or alkaline earth metal cations; (d) a source of a structure directing agent (SDA); (e) a source of hydroxide ions; and (f) water;
(2) forming aluminosilicate molecular sieve crystals having an STA-30 framework and the structure directing agent, and
(3) recovering at least a portion of the aluminosilicate molecular sieve crystals from the reaction mixture.

14. The method of claim 13, wherein the SDA comprises one or more 1,4-diazabicyclo[2.2.2]octane and 1-azabicyclo[2.2.2]octane dications derivates.

15. The method of claim 13, where the source of hydroxide ions comprise an alkyl quaternary ammonium compound.

16. The method of claim 13, wherein the reaction mixture has one or more of the following compositional molar ratios:

| | |
|---|---|
| $SiO_2/Al_2O_3$ | 10-100 |
| $Z_2O/SiO_2$ | 0.01-1.0 |
| $SDA/SiO_2$ | 0.01-0.8 |
| $OH/SiO_2 2$ | 0.1-1.0 |
| $H_2O/SiO_2$ | 8-80. | wherein Z represents the alkali metal or alkaline earth metal.

17. A method or treating an exhaust gas comprising contacting a combustion exhaust gas containing $NO_x$ and/or $NH_3$ with a catalyst according to claim 9 to selectively reduce at least a portion of the $NO_x$ into $N_2$ and $H_2O$ and/or oxidize at least a portion of the $NH_3$.

18. A method for treating an exhaust gas comprising contacting a combustion exhaust gas containing $NO_x$ with a passive $NO_x$ absorber comprising the molecular sieve of claim 1.

19. A method of converting methanol to an olefin (MTO) comprising contacting methanol with the molecular sieve of according to claim 1.

20. The molecular sieve of claim 1, where the molecular sieve further comprises at least one extra-framework transition metal selected from the group consisting of Cu, Fe, Co and Ni.

* * * * *